(12) United States Patent
Green et al.

(10) Patent No.: US 7,309,817 B2
(45) Date of Patent: Dec. 18, 2007

(54) PLANT ALPHA FARNESENE SYNTHASE AND POLYNUCLEOTIDES ENCODING SAME

(75) Inventors: Sol Alexander Green, Takapuna (NZ); Ellen Nicola Friel, Western Springs (NZ); Lesley Leah Beuning, Huapai (NZ); Elspeth Ann Macrae, Mt. Albert (NZ)

(73) Assignee: The Horticulture and Food Research Institute of New Zealand Limited, Auckland (NZ)

( * ) Notice: Subject to any disclaimer, the term of this patent is extended or adjusted under 35 U.S.C. 154(b) by 113 days.

(21) Appl. No.: 10/531,357

(22) PCT Filed: Oct. 15, 2003

(86) PCT No.: PCT/NZ03/00229

§ 371 (c)(1),
(2), (4) Date: Sep. 22, 2005

(87) PCT Pub. No.: WO2004/035791

PCT Pub. Date: Apr. 29, 2004

(65) Prior Publication Data

US 2006/0137032 A1  Jun. 22, 2006

(30) Foreign Application Priority Data

Oct. 15, 2002 (NZ) ........................ 521984

(51) Int. Cl.
| | |
|---|---|
| *A01H 1/00* | (2006.01) |
| *C07H 21/04* | (2006.01) |
| *C12N 15/29* | (2006.01) |
| *C12N 15/52* | (2006.01) |
| *C07K 14/415* | (2006.01) |

(52) U.S. Cl. .................. 800/295; 435/6; 435/69.1; 435/468; 435/419; 435/252.3; 435/320.1; 435/183; 530/370; 800/278; 536/23.6

(58) Field of Classification Search .............. 435/6, 435/69.1, 468, 419, 252.3, 320.1, 183; 530/370; 536/23.6; 800/278
See application file for complete search history.

(56) References Cited

U.S. PATENT DOCUMENTS

| | | | |
|---|---|---|---|
| 5,264,558 A | 11/1993 | Kim et al. | |
| 5,487,983 A | 1/1996 | Kim et al. | |
| 5,871,988 A * | 2/1999 | Croteau et al. | ............. 435/183 |
| 6,008,043 A | 12/1999 | Croteau et al. | |

FOREIGN PATENT DOCUMENTS

| | | |
|---|---|---|
| JP | 2000245482 | 9/2000 |
| WO | WO 99/15624 | 4/1999 |
| WO | WO 99/18118 | 4/1999 |
| WO | WO 00/17327 | 3/2000 |
| WO | WO0164835 A2 * | 9/2001 |

OTHER PUBLICATIONS

Database EMBL (2003) "Malus x domestica (E,E)-α-farnesene synthase (AFS1) mRNA, complete cds." EBI accession No. EMBL:AY182241.
Green, S. et al. (2007) "Unusual features of a recombinant apple α-farnesene synthase"; Phytochemistry 68(2):176-188.
Pechous, S.W. et al. (2004) "Cloning and functional expression of an (E,E)-α-farnesene synthase cDNA from peel tissue of apple fruit"; Planta 219(1):84-94.
Phillips, M.A. et al. (2003) "cDNA isolation, functional expression, and characterization of (+)-α-pinene synthase and (−)-α-pinene synthase from loblolly pine (*Pinus taeda*): Stereocontrol in pinene biosynthesis"; Archives of Biochemistry and Biophysics 411(2):267-276.
Altschul et al. (1997) "Gapped BLAST and PSI-BLAST: A New Generation of Protein Database Search Programs," *Nuc. Acids Res.* 25(17):3389-3402.
Bengtsson et al. (2001) "Plant Odor Analysis of Apple: Antennal Response of Codling Moth Female to Apple Volatiles during Phenological Development," *J. Agric. Food Chem.* 49:3736-3741.
Benfey et al. (1989) "Regualted Genes in Transgenic Plants," *Science* 244:174-181.
Bohlmann et al. (1998) "Plant Terpenoid Synthases: Molecular Biology and Phylogenetic Analysis," *Proc. Natl. Acad. Sci. USA* 95:4126-4133.
Cai et al. (2002) "A cDNA Clone for β-Caryophyllene Synthase from *Artemisia annual*," *Phytochem.* 61:523-529.
Cane et al. (1999) "Trichodiene Synthase: Mechanism-Based Inhibition of a Sesquiterpene Cyclase," *Bioorg. Med. Chem. Lett.* 9:1127-1132.
Chen et al. (1996) "Cloning and heterologous expression of a second (+)-delta-cadinene synthase for *Gossypium arboreum*"; *J. Nat. Prod.* 59(10):944-951 (Abstract only).
Croteau et al. (2000) *Biochemistry and Molecular Biology of Plants*, Buchanan et al. Eds., American Society for Plant Physiologists, pp. 1250-1318.
Davies (1990) "Gas Chromatographic Retention Indices of Monoterpenes and Sesquiterpenes on Methyl Silicone and Carbowax 20M Phases," *J. Chrom.* 503:1-24.
Davis et al. (2000) "Cyclization Enzymes in the Biosynthesis of Monoterpenes, Sesquiterpines, and Diterpines," *Top. Curr. Chem.* 209:53-95.
Dellaporta et al. (1983) "A Plant DNA Minipreparation: Version II," *Plant Mol. Biol. Reporter* 1(4):19-21.
Duderava et al. (2003) "(*E*)-β-Ocimene and Myrcene Synthase Genes of Floral Scent Biosynthesis in Snapdragon: Function and Expression of Three Terpene Synthase Genes of a New Terpene Synthase Subfamily," *Plant Cell* 15:1227-1241.

(Continued)

*Primary Examiner*—Phuong T Bui
(74) *Attorney, Agent, or Firm*—Greenlee Winner and Sullivan, PC

(57) ABSTRACT

The present invention provides an isolated alpha-farnesene synthase and polynucleotide sequences encoding the enzyme. The invention also provides nucleic acid constructs, vectors and host cells incorporating the polynucleotide sequences. It further relates to the production of alpha-farnesene using the enzyme and modulation of alpha-farnesene synthesis in plants and selection of plants with altered alpha-farnesene synthase activity.

15 Claims, 21 Drawing Sheets

OTHER PUBLICATIONS

Emanuelsson et al. (2000) "Predicting Subcellular Localization of Proteins Based on their N-terminal Amino Acid Sequence," *J. Mol. Biol.* 300:1005-1016.

Fan et al. (1999) "Development of Apple Superficial Scald, Soft Scald, Core Flush, and Greasiness Is Reduced by MCP," *J. Agric. Food Chem.* 47:3063-3068.

Fischbach (2001) "Putative Chloroplast Terpene Synthase," *Genbank* CAC41012.

Ju et al. (2000) "Cuticular Phenolics and Scald Development in "Delicious" Apples," *J. Am. Soc. Hortic. Sci.* 125(4):498-504.

Ju et al. (2000) "Lovastatin Inhibits α-Farnesene Biosynthesis and Scald Development in "Delicious" and "Granny Smith" Apples and "d'Anjou" Pears," *J. Am. Soc. Hortic. Sci.* 125(5):626-629.

Ju et al. (2000) "Lovastatin Inhibits α-Farnesene Synthesis Without Affecting Ethylene Production During Fruit Ripening in "Golden Supreme" Apples," *J. Am. Soc. Hortic. Sci.* 125(1):105-110.

Ju et al. (2001) "Lovastatin Inhibition of α-Farnesene Production in Ripening Apple: Precursor Feeding Studies," *J. Am. Soc. Hortic. Sci.* 126(4):491-495.

Ju et al. (2000) "Evidence that α-Farnesene Biosynthesis During Fruit Ripening is Mediated by Ethylene Regulated Gene Expression in Apples," *Postharvest Biol. Technol.* 19:9-16.

Kawasaki et al. (1996) "Specific Regulation of Gene Expression by Antisense Nucleic Acids: A Summary of Methodologies and Associated Problems," *Artific. Organs* 20(8):836-848.

Lange et al. (2000) "Isoprenoid Biosynthesis: The Evolution of Two Ancient and Distinct Pathways Across Genomes," *Proc. Natl. Acad. Sci. USA* 97(24):13172-13177.

Langenkamper et al. (1998) "Sucrose-Phosphate Synthase Steady-State mRNA Increases in Ripening Kiwifruit," *Plant Mol. Biol.* 36:857-869.

Lesburg et al. (1998) "Managing and Manipulating Carbocations in Biology: Terpenoid Cyclase Structure and Mechanism," *Curr. Opin. Struct. Biol.* 8:695-703.

Llave et al. (2002) "Cleavage of *Scarecrom-like* mRNA Targets Directed by a Class of *Arabidopsis* miRNA," *Science* 297:2053-2056.

Lucker et al (2002) "Citrus limon" *Genbank* AF514288.

Leuhrsen (1991) "Intron Enhancement of Gene Expression and the Splicing Efficiency of Introns in Maize Cells," *Mol. Gen. Genet.* 225:81-93.

Matich et al. (1996) "Solid Phase Microextraction for Quantitative Headspace Sampling of Apple Volatiles," *Anal. Chem.* 68:4114-4118.

McIntyre (1996) "Strategies for the Suppression of Peroxidase Gene Expression in Tobacco. I. Designing Efficient Ribozymes," *Trans. Res.* 5:257-262.

Napoli et al. (1990) "Introduction of a Chimeric Chalcone Synthase Gene into Petunia Results in Reversible Co-Suppression of Homologous Genes in Trans," *Plant Cell* 2:279-290.

Needleman et al. (1970) "A General Method Applicable to the Search for Similarities in the Amino Acid Sequence of Two Proteins," *J. Mol. Biol.* 48:443-453.

Niebel et al. (1995) "Post-Transcriptional Cosuppression of [beta]-1,3-Glucanase Genes Does Not Affect Accumulation of Transgene Nuclear mRNA," *Plant Cell.* 7:347-358.

Pearson et al. (1988) "Improved Tools for Biological Sequence Comparison," *Proc. Natl. Acad. Sci. USA* 85:2444-2448.

Pearson (1990) "Rapid and Sensitive Sequence Comparison with FASTP and FASTA," *Methods in Enzymol.* 183:63-98.

Pechous et al. (2002) "Cloning and Functional Expression of an (E,E)-Alpha-Farnesene Synthase cDNA from Peel Tissue of Apple Fruit," *Genepept Accession* #AAO22848.

Robinson-Benion et al. (1995) "Antisence Techniques," *Methods in Enzymol.* 254:363-375.

Rowan et al. (2001) "Conjugated Triene Oxidation Products of α-Farnesene Induce Symptoms of Superficial Scald on Stored Apples," *J. Agric. Food. Chem.* 49:2780-2787.

Rupasinghe et al. (1998) "Biosynthesis of α-Farnesene and Its Relation to Superficial Scald Development in "Delicious" Apples," *J. Am. Soc. Hortic. Sci.* 123(5):882-886.

Rupasinghe et al. (2000) "Sesquiterpene α-Farnesene Synthase: Partial Purification, Characterization, and Activity in Relation to Superficial Scald Development in Apples," *J. Am. Soc. Hortic. Sci.* 125(1):111-119.

Shelton et al. (2003) "Putative Monoterpene Synthase," *Genbank* AAP40638.

Steele et al. (1998) "Sesquiterpene Synthases from Grand Fir (*Abies grandis*)," *J. Biol. Chem.* 273(4):2078-2089.

Trapp et al. (2001) "Genomic Organizaiton of Plant Terpene Synthases and Molecular Evolutionary Implications," *Genetics* 158:811-832.

Van Geldre et al. (2000) "Cloning and Molecular Analysis of Two New Sesquiterpene Cyclases from *Artemisia annua* L," *Plant. Sci.* 158:163-171.

Voinnet et al. (2003) "An Enhanced Transient Expression System in Plants Based on Suppression of Gene Silencing by the p19 Protein of Tomato Bushy Stunt Virus," *Plant J.* 33:949-956.

Watkins et al. (1993) "Relationships Between Alpha-Farnase, Ethylene Production and Superficial Scald Development of Apples," *Acta. Hort.* 343:155-160.

Whitaker et al. (2000) "Temperature-Dependent Autoxidation of Conjugated Trienols from Apple Peel Yields 6-Methyl-5-hepten-2-one, a Volatile Implicated in Induction of Scald," *J. Agric. Food. Chem.* 48:2040-2043.

Yang et al. (2002) "Geraniol Synthase," *Genbank* CAD29734.

Zubay et al. (1973) "In Vitro Synthesis of Protein in Microbial Systems," *Annu. Rev. Genet.* 7:267-287.

\* cited by examiner

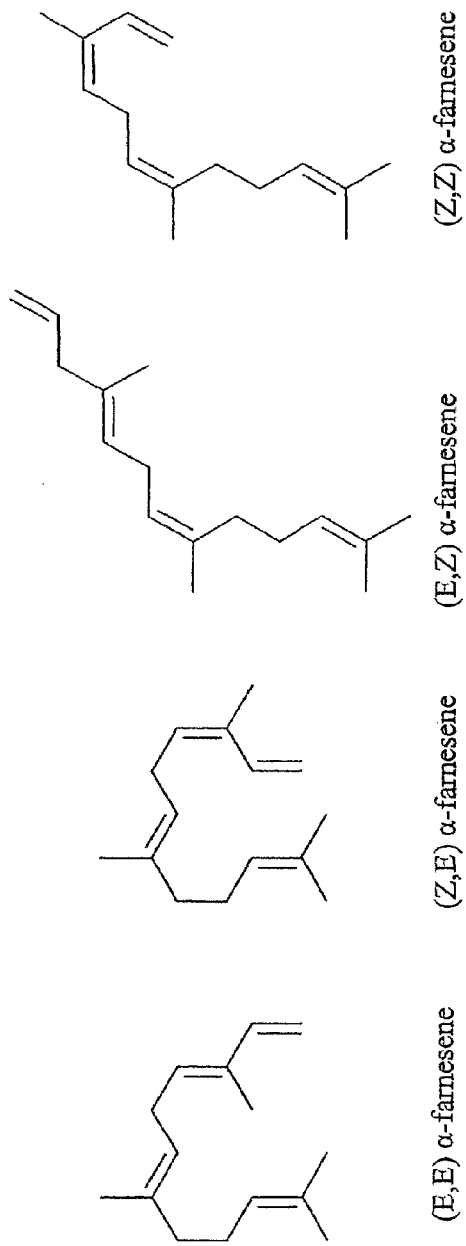
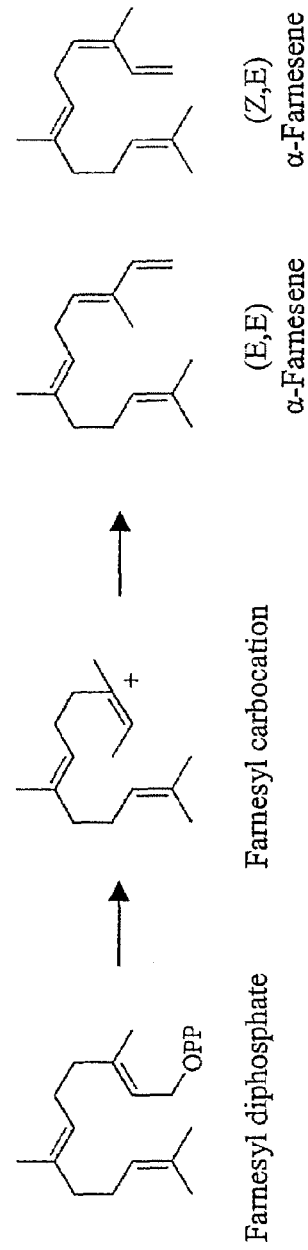
FIGURE 1
FIGURE 2

```
   1 CTATAGCTTC TTGTATCCCA AACATCTCGA GCTTCTTGTA CACCAAATTA GGTATTCACT ATGGAATTCA GAGTTCACTT CCAACCTGAT AATCAGCAGA
 101 AAATTTTTCA AAACCAGAATG AAACCCGAAC CTGAAGCCTC TTACTTGATT ATCGGAAGCC CCTCTCCAAA GCTCTCCAAA TTACAAGCCA AATATTCGA AGAACGATTT
 201 CCTAGATCAA TCTCTTATCA GCAAATACCA TGGAGATGAG TATCGGAAGC GAAAACTAGG TCTCTGAGAA GTTAATAGAA GAAGTTAACA TTTATATATC TGCTCAAACA
 301 ATCCATTTAC TAGCTAAGTT CGAACCTCAT GACACGCTCC GAAACCGTCC CCTCCGAAC CCATTACACT TCAAGATCCT CAGGCAGCAT GGCTATAAAG CACAGCCATTG
 401 CAGCTATCCA AAGCCACACA CTCGGCACAA GAGACGATCT CTATGGTACT GCATTACACT TCCCCCATTT AAAAGCAATG CTGAACTTTT TCGAGGCCTC AAACCTGGGT
 501 TATATTTGGT AGATTCATGG ATGAAAAGGG CACATTAGAC AACCACCATT TGACCCTAGC TCTCAGAGAT AGTGGTCATA TTTGTTATCC AGACAGTAAC CTTCCAGGG
 601 TTCCAAGGTC AAGATATTTT AGATGAGGGC AAAGCTTCCT ACCCAGAGT GCAGTGGTTT GGCAAATCAA CGCCTATGAA AAGACATTT GTCGCGTCAA
 701 ACCTAGTTCA TTCCCTGGAC CTTCCATCAC ACCCAGAGT GCAGTGGTTT GGCAAATCAA CGCCTATGAA AAGACATTT GTCGCGTCAA AAATCTGGCC
 801 CCCCACGTTA CTCGAATTAG CAAAGCTTAA TTTCAACGTA GTTCAGCCCC AACTCCAAAA AAACTTAAGG GAAGCATCCA GGTGGTAGCC CCACTCATCT TTTACAAATAT
 901 TTCCAGACA ACTTGAAATT TCCAAGAGAT AGACTGGTTG AATGTTCTC ATGTCCTCGTG GGAGTAGCAT TCGAGCCCTCA GCTAAGCAC TTCACCAATG CTGTGATAG
1001 GTCTTACCAA AGTCATCAAC TTAGTACTGA TCATAGACGA CGTCTATCGT ATTTATCGCT CAGACCAACA GCTAAGCAC ACTTGTGAAA TTGCTCGTCA AATTCAGGAG
1101 CTGCCATTCT ACGGAAACTG AGCACCTTCC AGATGCTATC AAGATGTGTT TCCAACTACT AAGATGTGAAA TGGAGGCAGA CTGGTATATAT AAGCCCATA
1201 GACAATGGTT CGAACCAAGT ATTACCTCAA TTGACCAAAG TGTGGGCAGA TTTTTGTAAA TCAGTGCTTT TGCTTCACTC GTTTTTCT ATAACTCATG ACGGAACCAA
1301 TACCAACCCT TCAAGACTAC CTAAGAAACC GATCCATTTC ATCATCGAAT AGATCTTTTG CCACCATCCT GTCTTTACTA TCCCCTCAAC AATGATTTGG GAACTTCCCC GGCTGAACAA
1401 AGAGATGGCT GATTTCTTC ACAAGAATGA AGATCTTTG TATAATATCT CTCTCATCGT TCCCCTCAAC AATGATTTGG GAACTTCCCC GGCTGAACAA
1501 GAGAGAGGG ATTCCCTTC ATCAATGTA TGTTACATGA GAGAAGTGAA TGCCTCTGAA GAAACAGCTA GGAAGAACAT TAAGGGGATG ATAGACAATG
1601 CATGCAAGAA ACTAAATGGA AAATGCTTCA CAACAAACCA ACTGCCTTTT CTGTCATCAT TCATGAACAA TGCCACAAAC ATGGCACGTG TGGCCACAG
1701 CCTTTACAAA GATGGAGATG GTTTTGGTCA CCAAGACAAA GGGCCTCGGA CCCACATCCT GTCTTTACTA TTCCAACCTC TTGTAAACTA CTACTATAT
1801 AGTTGAAAT AAATAGCAGC AAGAAGTTTG CGGTTCAGTT CGTCATGGAT AAATAATCT TTACAGTTTC TAACCTTGTT CCACAAACAT TATCAATAAA
1901 AAGTTCTAGT TTCTCGTTTA TTTTTAAAA AAAAAAAAA AA
```

FIGURE 3

| | | | | | |
|---|---|---|---|---|---|
| 1 | MEFRVHLQAD | NEQKIFQNQM | KPEPEASYLI | NQRRSANYKP | NIWKNDFLDQ |
| 50 | SLISKYDGDE | YRKLSEKLIE | EVKIYISAET | MDLVAKLELI | DSVRKLGLAN |
| 100 | LFEKEIKEAL | DSIAAIESDN | LGTRDDLYGT | ALHFKILRQH | GYKVSQDIFG |
| 150 | RFMDEKGTLE | NHHFAHLKGM | LELFEASNLG | FEGEDILDEA | KASLTLALRD |
| 200 | SGHICYPDSN | LSRDVVHSLE | LPSHRRVQWF | DVKWQINAYE | KDICRVNATL |
| 250 | LELAKLNFNV | VQAQLQKNLR | EASRWWANLG | FADNLKFARD | RLVECFSCAV |
| 300 | GVAFEPEHSS | FRICLTKVIN | LVLIIDDVYD | IYGSEEELKH | FTNAVDRWDS |
| 350 | RETEQLPECM | KMCFQVLYNT | TCEIAREIEE | ENGWNQVLPQ | LTKVWADFCK |
| 400 | ALLVEAEWYN | KSHIPTLEEY | LRNGCISSSV | SVLLVHSFFS | ITHEGTKEMA |
| 450 | DFLHKNEDLL | YNISLIVR<u>LN</u> | <u>NDLGTSAAEQ</u> | ERGDSPSSIV | CYMREVNASE |
| 500 | ETARKNIKGM | IDNAWKKVNG | KCFTTNQVPF | LSSFMNNATN | MARVAHSLYK |
| 550 | DGDGFGDQEK | GPRTHILSLL | FQPLVN* | | |

FIGURE 4

PLANT ALPHA FARNESENE SYNTHASE AND POLYNUCLEOTIDES ENCODING SAME

CROSS REFERENCE TO RELATED APPLICATIONS

This application is a National Stage Application of PCT International Application No. PCT/NZ2003/000229, filed on Oct. 15, 2003, which claims benefit of NZ 521984, filed on Oct. 15, 2002, which is incorporated herein by reference in its entirety.

TECHNICAL FIELD

The present invention relates to the enzyme alpha-farnesene synthase and to polynucleotide sequences encoding the enzyme. The invention also relates to nucleic acid constructs, vectors and host cells incorporating the polynucleotide sequences. It further relates to the production of alpha-farnesene and its use in products such as an insect attractant, a sex pheromone and other products. Alpha-farnesene may also be used to produce other products with characteristic aromas useful as flavours and fragrances.

BACKGROUND ART

Alpha-farnesene (FIG. 1) is an acyclic sesquiterpene hydrocarbon ($C_{15}H_{24}$; 3,7,11-trimethyl-1,3,6,10-dodecatetraene) that is either constitutively present or induced in a wide range of species.

The biosynthetic pathway for the sesquiterpenes branches off from the general terpenoid pathway, beginning with the allylic diphosphate ester farnesyl diphosphate (FDP, also shortened to FPP) (Bohlmann, et al., Proc. Natl. Acad. Sci. U.S.A. 95, 4126-4133 (1998), Cane and Bowser, Bioorg. Med. Chem. Lett. 9, 1127-1132 (1999), Davis and Croteau, Top. Curr. Chem. 209, 53-95 (2000)). Alpha-farnesene is synthesised from FDP in a reaction that proceeds through a carbocation intermediate (FIG. 2) and is catalysed by the sesquiterpene synthase alpha-farnesene synthase (Rupasinghe, et al., J. Am. Soc. Hortic. Sci. 123, 882-886 (1998)). The pathway for sesquiterpene biosynthesis, the acetate/mevalonate pathway, is localised to the cytoplasm; in contrast to the pathways for monoterpene and diterpene biosynthesis, which occur in the chloroplast (Croteau, et al., In Biochemistry and Molecular Biology of Plants, eds Buchanan, Gruissem and Jones, American Society of Plant Physiologists, 1250-1318 (2000); Lange, et al., Proc. Natl. Acad. Sci. U.S.A. 97, 13172-13177 (2000)).

All known plant terpene synthases, however, whether monoterpene, sesquiterpene or diterpene, appear to be closely related. Similarities include the positioning of intron sequences (Trapp and Croteau, Genetics 158, 811-832 (2001)) and the presence of conserved sequences, such as an aspartate-rich DDXX(D,E) motif (Lesburg, et al., Curr. Opin. Struct. Biol. 8, 695-703 (1998)). This motif is involved in the binding of metal ions, usually $Mg^{2+}$, that are necessary for catalysis. (Lesburg, et al., Curr. Opin. Struct. Biol. 8, 695-703 (1998)).

Alpha-farnesene synthase has been partially purified from the skin of apple fruit (*Malus domestica* Delicious). However, poor recovery and instability of the partially purified enzyme restricted further purification (Rupasinghe, et al., J. Am. Soc. Hortic. 125, 111-119 (2000)).

Alpha-farnesene is an insect attractant. It is a sex pheromone in mice and insects. Oxygenated (including chemicals occurring on exposure to air) alpha-farnesene products (eg farnesol, farnesal) have characteristic aromas (flavour/fragrance use). Other uses for alpha-farnesene and its derivatives are as potent cancer prevention agents, and in plastic film synthesis.

There is also a link between both the levels of alpha-farnesene and its oxidation products and the development of superficial scald, a postharvest physiological disorder that appears as a dark coloration of the apple skin following cool storage (Watkins, et al., Acta Hort. 343, 155-160 (1993), Ju and Bramlage, J. Am. Soc. Hortic. Sci. 125, 498-504 (2000), Whitaker and Saftner, J. Agric. Food Chem. 48, 2040-2043 (2000), Rowan, et al., J. Agric. Food Chem. 49, 2780-2787 (2001)). To date the causal relationship between alpha-farnesene and scald is still unclear (Ju and Curry, J. Am. Soc. Hortic. Sci. 125, 626-629 (2000), Rupasinghe, et al., J. Am. Soc. Hortic. Sci. 125, 111-119 (2000)). Ethylene production and alpha-farnesene biosynthesis also appear to be closely associated (Watkins, et al., Acta Hort. 343, 155-160 (1993), Fan, et al., J. Agric. Food Chem. 47, 3063-3068 (1999)). Recently it has been shown that ethylene may regulate the biosynthesis of alpha-farnesene during fruit ripening by acting on the mevalonate pathway, specifically by inducing the conversion of hydroxymethylglutaryl CoA to mevalonic acid (Ju and Curry, J. Am. Soc. Hortic. Sci. 125, 105-110 (2000), Ju and Curry, Postharvest Biol. Technol. 19, 9-16 (2000), Ju and Curry, J. Am. Soc. Hortic. Sci. 126, 491-495 (2001)).

It is an object of the invention to provide methods for in vitro synthesis of alpha-farnesene and/or for genetically modifying plants to alter the levels of alpha-farnesene synthase activities in plants; and/or to offer the public a useful choice.

SUMMARY OF THE INVENTION

In a first aspect the invention provides an isolated polynucleotide encoding alpha-farnesene synthase. In a preferred embodiment the polynucleotide encodes a polypeptide comprising at least one repeat of DDXXD and (L,V)(V,L,A)(N,D)(L,I,V)X(S,T)XXXE, wherein X is any amino acid.

In a further aspect the invention provides an isolated polynucleotide of SEQ ID NO:1 also (shown in FIG. 3) or a fragment or variant thereof wherein the fragment or variant encodes a polypeptide with alpha-farnesene synthase activity.

In a further aspect, the invention provides an isolated polynucleotide encoding the polypeptide of SEQ ID NO:2 (shown in FIG. 4) or encoding a variant or a fragment of that sequence which has alpha-farnesene synthase activity.

In a further aspect the invention provides an isolated alpha-farnesene synthase polypeptide.

In yet a further aspect, the invention provides an isolated alpha-farnesene synthase having the sequence SEQ ID NO:2 or a fragment or variant thereof with alpha-farnesene synthase activity.

The polypeptides of the invention are useful for in vitro preparation of alpha-farnesene.

In a further aspect the invention provides a genetic construct comprising a polynucleotide of the invention.

In yet a further aspect the invention provides a genetic construct comprising in the 5'-3' direction an open reading frame polynucleotide encoding a polypeptide of the invention.

Preferably the genetic construct also comprises a promoter sequence.

Preferably the genetic construct further comprises a termination sequence.

In another aspect the invention provides a genetic construct comprising in the 5'-3' direction a polynucleotide which hybridizes to a polynucleotide encoding a polypeptide of the invention.

Preferably the genetic construct also comprises a promoter sequence.

Preferably the genetic construct further comprises a termination sequence.

In a further aspect the invention provides a vector comprising a genetic construct of the invention.

In a further aspect the invention provides a host cell comprising a genetic construct of the invention.

In still a further aspect, the invention provides a transgenic plant cell which includes a genetic construct of the invention.

In addition the invention provides a transgenic plant comprising such cells.

In another aspect the invention provides a method for preparing alpha-farnesene comprising the steps of
(a) culturing a cell which has been genetically modified with a polynucleotide of the invention to provide increased alpha-farnesene synthase activity;
(b) providing the cell with farnesyl diphosphate if necessary; and
(c) separating the alpha-farnesene produced.

This method of the invention allows use of biofermentation for a convenient method for preparing the product.

In a further aspect the invention provides a method for preparing alpha-farnesene comprising the steps of
(a) obtaining a polypeptide of the invention
(b) incubating farnesyl diphosphate in the presence of the polypeptide and
(c) separating the alpha-farnesene produced.

In a further aspect the invention comprises a method for modulating the alpha-farnesene production of a plant, the method comprising: increasing or decreasing expression of alpha-farnesene synthase wherein said increasing or decreasing is achieved by genetic modification to alter the expression of a gene encoding an alpha-farnesene synthase. The modified cell and plants comprising such a cell also form part of the invention.

In a further aspect the invention there is provided a polynucleotide comprising at least 15 contiguous nucleotides from SEQ ID NO: 1

In a further aspect the invention comprises a method of selecting a plant with altered alpha-farnesene content comprising the steps of:
(a) contacting polynucleotides from at least one plant with at least one polynucleotide comprising at least 15 contiguous nucleotides of the polynucleotide of claim 1 to assess the expression of alpha-farnesene synthase; and
(b) selecting a plant showing altered expression.

BRIEF DESCRIPTION OF DRAWINGS

The present invention will be better understood with reference to the accompanying drawings in which:

FIG. 1 shows the structures of the isomers of alpha-farnesene.

FIG. 2 shows the pathway for alpha-farnesene synthesis in apple.

FIG. 3 shows the cDNA sequence that encodes alpha-farnesene synthase. The sequence was obtained from a cDNA library that was constructed from Royal Gala 150 days after full bloom (DAFB) apple skin.

FIG. 4 shows the predicted amino acid sequence of alpha-farnesene synthase from apple skins. The DDXXD motif involved in the binding of the metal ions necessary for catalysis is in bold. The highly conserved consensus sequence (L,V)(V,L,A)(N,D)D(L,I,V)X(S,T)XXXE, also involved in metal ion binding, is underlined.

DETAILED DESCRIPTION

Figure 5:
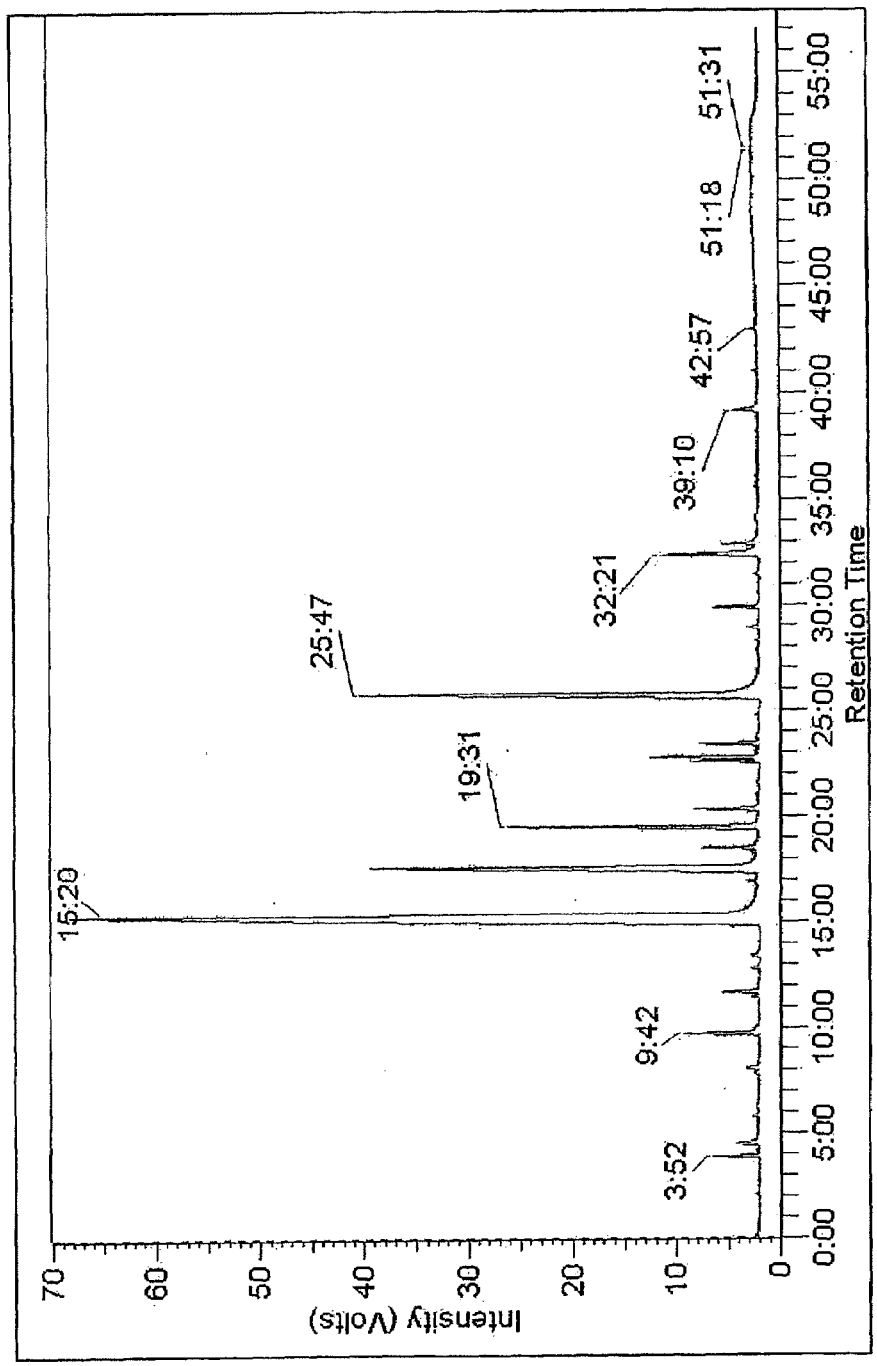
FIG. 5 shows a GC-MS trace of headspace above Royal Gala apples showing (E,E) alpha-farnesene peak at retention time 42.57 minutes.

In one embodiment of the invention, cells genetically modified to exhibit alpha-farnesene synthase activity are used for the production of alpha-farnesene. While the cells may potentially be of any cell type that can be grown in culture, it is currently preferred to use bacteria or yeast cells for producing alpha-farnesene (and its oxidation products or derivatives). Preferred cells for use in the biofermentation processes of this embodiment are cells with GRAS status, for example appropriate *E. coli* strains, *Lactobacillus* sp and other non-pathogenic GRAS status bacteria or yeasts such as brewers yeast.

Alpha-farnesene (or derivatives of alpha-farnesene) produced by biofermentation may be used as pheromones for use in insect or rodent control; as flavour or fragrance additives to food, medicine, toothpastes or perfumes; for the manufacture of pharmaceuticals with anti-tumour, anti-candida, mucosal stabilizing, anti-inflammatory and anti-ulcerative properties, for the manufacture of films and polymers for use in packaging and moulded articles, particularly degradable plastics, general agrochemical production, production of solvents for industrial cleaning (eg algaecides) and membranes for dewaxing solvents or oils.

In an alternative to alpha-farnesene production by biofermentation, alpha-farnesene synthase may be extracted and optionally immobilised and used in alpha-farnesene production. For example cultured cells as described above may be used as the source of alpha-farnesene synthase. The enzyme may for example be immobilised on beads, for example alginate beads.

In another aspect of the invention, the polynucleotides of the invention are used to prepare transgenic plants that over-express the alpha-farnesene synthase in at least some parts of the plant. In this way the invention is used to impart fragrance to flowers, to repel or attract insects (either as indicator plants, host plants, or alternative hosts) or to impart an altered flavour to fruit or vegetables or to prevent scald in fruit, or to extract pharmaceutical products or animal or insect efficacious extracts.

In one particular aspect the polynucleotides of the invention are used in plants of the order Rosaceae, particularly in the genus *Malus* to provide increased flavour in fruit.

In another aspect polynucleotides of the invention are used to decrease alpha-farnesene synthase activity in apple fruit. This may be achieved in several ways, for example by genetically modifying the apples so that alpha-farnesene synthase polynucleotide is transcribed in an antisense orientation which results in decreased alpha-farnesene synthase translation. Such fruit may then display decreased superficial scald in apple skin following cold storage or be less attractive to insects such as the codling moth.

In another aspect the invention provides a method useful in apple breeding. Segments of the polynucleotide sequences of the invention may be used as probes or primers to investigate the genetic makeup of candidate apple varieties with respect to alpha-farnesene synthase activity. The presence of high levels of polynucleotides encoding alpha-farnesene synthase activity in the fruit of apples may be used to identify apples with added flavour and presence of low levels may be used to identify apples with favourable storage properties or insect resistance.

The amino acid sequence of one polypeptide, an alpha-farnesene synthase from apple, and that of the polynucleotide sequence encoding it are given in FIGS. 4 and 3 respectively (SEQ ID NO:2 and SEQ ID NO:1). It will however be appreciated that the invention is not restricted only to the polynucleotide/polypeptide having the specific nucleotide/amino acid sequence given in FIGS. 3 and 4. Instead, the invention also extends to variants of the polynucleotide/polypeptide of FIGS. 3 and 4 which encode or possess alpha farnesene synthase activity.

The term "polynucleotide(s)" as used herein means a single or double-stranded polymer of deoxyribonucleotide or ribonucleotide bases and includes DNA and corresponding RNA molecules, including hnRNA and mRNA molecules, both sense and anti-sense strands, and comprehends cDNA, genomic DNA and recombinant DNA, as well as wholly or partially synthesized polynucleotides. An hnRNA molecule contains introns and corresponds to a DNA molecule in a generally one-to-one manner. An mRNA molecule corresponds to an hnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments.

The term 'polypeptide(s)' as used herein includes peptides, polypeptides and proteins.

The phrase "variants with alpha-farnesene synthase activity" is used in recognition that it is possible to vary the amino acid/nucleotide sequence of a polypeptide/polynucleotide while retaining substantially equivalent functionality. The equivalent can be, for example, a fragment of the polypeptide, a fusion of the polypeptide with another polypeptide or carrier, or a fusion of a fragment with additional amino acids.

An "isolated" polypeptide is a polypeptide that has been identified and separated or recovered to be largely free of components of its natural environment, (that is so that the polypeptide comprises at least 50% of the polypeptides from its natural environment, preferably at least 80%, more preferably at least 90%). The term "isolated" polypeptide includes polypeptides in situ within recombinant cells. However generally isolated polypeptides will be prepared by at least one purification step.

An "isolated" polynucleotide is a nucleotide molecule that is identified and separated from at least one contaminant polynucleotide with which it is ordinarily associated.

Variant polynucleotide sequences also include equivalent sequences, which vary in size, composition, position and number of introns, as well as size and composition of untranslated terminal regions. Variant polynucleotides also include those encoding functionally equivalent polypeptides.

It will be understood that a variety of substitutions of amino acids is possible while preserving the structure responsible for activity of the polypeptides. Conservative substitutions are described in the patent literature, as for example, in U.S. Pat. No. 5,264,558 or U.S. Pat. No. 5,487,983. It is thus expected, for example, that interchange among non-polar aliphatic neutral amino acids, glycine, alanine, proline, valine and isoleucine, would be possible. Likewise, substitutions among the polar aliphatic neutral amino acids, serine, threonine, methionine, asparagine and glutamine could be made. Substitutions among the charged acidic amino acids, aspartic acid and glutamic acid, could probably be made, as could substitutions among the charged basic amino acids, lysine and arginine. Substitutions among the aromatic amino acids, including phenylalanine, histidine, tryptophan and tyrosine are also possible. Such substitutions and interchanges are well known to those skilled in the art.

Equally, nucleotide sequences encoding a particular product can vary significantly simply due to the degeneracy of the nucleic acid code.

A polynucleotide or polypeptide sequence may be aligned, and the percentage of identical nucleotides in a specified region may be determined against another sequence, using computer algorithms that are publicly available. Two exemplary algorithms for aligning and identifying the similarity of polynucleotide sequences are the BLASTN and FASTA algorithms. The similarity of polypeptide sequences may be examined using the BLASTP algorithm. Both the BLASTN and BLASTP software are available on the NCBI anonymous FPT server. The BLASTN algorithm version 2.0.4 [Feb.-24-1998], set to the default parameters described in the documentation of variants according to the present invention. The use of the BLAST family of algorithms, including BLASTN and BLASTP, is described at NCBI's website at URL and in the publication of Altschul et al., Nucleic Acids Res. 25, 3389-34023 (1997). The computer algorithm FASTA is available on the Internet. Version 2.0u4, February 1996, set to the default parameters described in the documentation and distributed with the algorithm, is also preferred for use in the determination of variants according to the present invention. The use of the FASTA algorithm is described in Pearson and Lipman Proc. Natl. Acad. Sci. USA 85, 2444-2448 (1988), Pearson Methods in Enzymology 183, 63-98 (1990).

The following running parameters are preferred for determination of alignments and similarities using BLASTN that contribute to E values (as discussed below) and percentage identity: Unix running command: blastall -p blastn -d embldb -e 10 -G 1 -E 1 -r 2 -v 50 -b 50 -I queryseq -o results; and parameter default values:
-p Program Name [String]
-d Database [String]
-e Expectation value (E) [Real]
-G Cost to open a gap (zero invokes default behaviour) [Integer]
-E Cost to extend a cap (zero invokes default behaviour) [Integer]
-r Reward for a nucleotide match (blastn only) [Integer]
-v Number of one-line descriptions (V) [Integer]
-b Number of alignments to show (B) [Integer]
-i Query File [File In]
-o BLAST report Output File [File Out] Optional For BLASTP the following running parameters are preferred: blastall -p blastp -d swissprotdb -e 10 -G 1 -E 1 -v 50 -b 50 -I queryseq -o results
-p Program Name [String]
-d Database [String]
-e Expectation value (E) [Real]
-G Cost to open a gap (zero invokes default behaviour) [Integer]
-E Cost to extend a cap (zero invokes default behaviour) [Integer]
-v Number of one-line descriptions (v) [Integer]
-b Number of alignments to show (b) [Integer]
-i Query File [File In]
-o BLAST report Output File [File Out] Optional The "hits" to one or more database sequences by a queried sequence produced by BLASTN, BLASTP, FASTA, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN and FASTA algorithms also produce "Expect" or E values for alignments. The E value indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a hit is interpreted as meaning that in a database of the size of the EMBL database, one might expect to see 0.1 matches over the aligned portion of the sequence with a similar score simply by chance. By this criterion, the aligned and matched portions of the sequences then have a 90% probability of being the same. For sequences having an E value of 0.01 or less over aligned and matched portions, the probability of finding a match by chance in the EMBL database is 1% or less using the BLASTN or FASTA algorithm.

According to one embodiment, "variant" polynucleotides, with reference to each of the polynucleotides of the present invention, preferably comprise sequences having the same number or fewer nucleic acids than each of the polynucleotides of the present invention and producing an E value of 0.01 or less when compared to the polynucleotide of the present invention. That is, a variant polynucleotide is any sequence that has at least a 99% probability of being the same as the polynucleotide of the present invention, measured as having an E value of 0.01 or less using the BLASTN or FASTA algorithms set at the parameters discussed above.

Variant polynucleotide sequences will generally hybridize to the recited polynucleotide sequence under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C. The variant polynucleotide sequences of the invention are at least 50 nucleotides in length.

Variant polynucleotides also include sequences which have a sequence identity of at least 25% or at least 60%, generally 70%, preferably 80%, more preferably 90%, even more preferably 95%, very preferably 98% and most preferably 99% or more to the nucleotide sequence given in the sequence listing herein.

In general, polypeptide sequences that code for the alpha-farnesene synthases of the invention will be at least 25% or at least 50%, generally at least 60%, preferably 70%, and even 80%, 85%, 90%, 95%, 98%, most preferably 99% homologous or more with the disclosed amino acid sequence. That is, the sequence similarity may range from 25% to 99% or more. In addition the invention includes polynucleotide sequences encoding these amino acid sequences.

Also encompassed by the invention are fragments of the polynucleotide and polypeptide sequences of the invention. Polynucleotide fragments may encode protein fragments which retain the biological activity of the native protein. Alternatively, fragments used as hybridisation probes generally do not encode biologically active sequences. Fragments of a polynucleotide may range from at least 15, 20, 30, 50, 100, 200, 400 or 1000 contiguous nucleotides up to the full length of the native polynucleotide sequences disclosed herein.

Fragments of the polypeptides of the invention will comprise at least 5, 10, 15, 30, 50, 75, 100, 150, 200, 400 or 500 contiguous amino acids, or up to the total number of amino acids in the full length polypeptides of the invention.

Variant is also intended to allow for rearrangement, shifting or swapping of one or more nucleotides or domains/motifs (from coding, non-coding or intron regions) from genes (including terpene synthases) from the same or other species, where such variants still provide a functionally equivalent protein or polypeptide of the invention or fragment thereof.

It is, of course, expressly contemplated that homologs to the specifically described alpha-farnesene synthase having the sequence of FIG. 4 (SEQ ID NO:2) exist in other plants. Such homologs are also "variants" as the phrase is used herein.

A polynucleotide sequence of the invention may further comprise one or more additional sequences encoding one or more additional polypeptides, or fragments thereof, so as to encode a fusion protein. Systems for such recombinant expression include, but are not limited to, mammalian, bacteria and insect expression systems. Also contemplated are cell-free expression systems.

DNA sequences from plants other than *Malus domestica* which are homologs of the alpha-farnesene synthase of FIG. 3 (SEQ ID NO:1) may be identified (for example by computer-aided searching of private or public and sequence databases. Alternatively, probes based on the sequence of FIG. 4 can be synthesized and used to identify positive clones in either cDNA or genomic DNA libraries derived from other plants by means of hybridization methods. PCR-based techniques including reverse-transcriptase (RT)-PCR may also be employed. Probes and/or PCR primers should be at least about 10, preferably at least about 15 and most preferably at least about 20 nucleotides in length. Hybridization and PCR techniques suitable for use with such oligonucleotide probes are well known in the art. Positive library clones or PCR products may be analyzed by restriction enzyme digestion, DNA sequencing or the like.

The polynucleotides of the present invention may be generated by synthetic means using techniques well known in the art. Equipment for automated synthesis of oligonucleotides is commercially available from suppliers such as Perkin Elmer/Applied Biosystems Division (Foster City, Calif.) and may be operated according to the manufacturer's instructions.

Allelic variation in *Malus domestica* has been observed. The alpha-farnesene synthase polypeptide of the variety Aotea differs from that of SEQ ID NO:2 by 5 amino acids over a partial sequence. Partial polynucleotide sequences for the alpha-farnesene synthase gene in Aotea and the corresponding polypeptide are those of SEQ ID NO:6 and SEQ ID NO: 7 respectively.

```
                                         (SEQ ID NO:6)
CTAAGTTGGAGCTCATTGACAGCGTCCGAAAACTAGGCCTCGCGAACCTC

TTCGAAAAGGAAATCAAGGAAGCCCTAGACAGCGTTGCAGCTATCGAAAG

CGACAATCTCGGCACAAGAGACGATCTCTATGCTACTGCATTACACTTCA

AGATCCTCAGGCAGCATGGCTATAAAGTTTCACAAGATATATTTGGTAGA

TTCATGGATGAAAAGGGCACATTAGAGAACCACCATTTCGCGCATTTAAA

AGGAATGCTGGAACTTTTCGAGGCCTCAAACCTGGGTTTCGAAGGTGAAG

ATATTTTAGATGAGGCGAAAGCTTCCTTGACGCTAGCTCTCAGAGATAGT

GGTCATATTTGTTATCCAGACAGTAACCTTTCCAGGGACGTAGTTCATTC

CCTGGAGCTTCCATCACACCGCAGAGTGCAGTGGTTTGATGTCAAATGGC

AAATCGACGCCTATGAAAAAGACATTTGTCGCGTCAACGCCACGTTACTC

GAATTAGCAAAGCTTAATTTCAACGTAGTTCAGGCCCAACTCCAAAAAAA

CTTAAGGGAAGCATCCAGGTGGTGGGCAAACCTGGGCATCGCAGACAACT

TGAAATTTGCAAGAGATAGACTGGTTGAATGTTTCGCATGTGCTGTGGGA

GtAGCATTCGAGCCAGAGCACTCATC (SEQ ID NO:7)
KLELIDSVRKLGLANLFEKEIKEALDSVAAIESDNLGTRDDLYATALHFK

ILRQHGYKVSQDIFGRFMDEKGTLENHHFAHLKGMLELFEASNLGFEGED

ILDEAKASLTLALRDSGHICYPDSNLSRDVVHSLELPSHRRVQWFDVKWQ

IDAYEKDICRVNATLLELAKLNFNVVQAQLQKNLREASRWWANLGIADNL

KFARDRLVECFACAVGVAFEPEHS
```

As a result of the identification of the polypeptides and polynucleotides of the invention alpha-farnesene activity may be modulated in plants. Modulation may involve a reduction in the expression and/or activity (i.e. silencing) of the polypeptide.

Any conventional technique for effecting such silencing can be employed. Intervention can occur post-transcriptionally or pre-transcriptionally. Further, intervention can be focused upon the gene itself or on regulatory elements associated with the gene and which have an effect on expression of the encoded polypeptide. "Regulatory elements" is used here in the widest possible sense and includes other genes which interact with the gene of interest.

Pre-transcription intervention can involve mutation of the gene itself or of its regulatory elements. Such mutations can be point mutations, frameshift mutations, insertion mutations or deletion mutations. So called "knock-out" mutations in which expression of the gene can be entirely ablated. Alternatively transposon tagging may be used. Another approach is to modify transcription through expression of a naturally occurring and/or artificial transcription factor, for example an artificial zinc finger protein transcription factor designed to interact with the endogenous promoter of the alpha-farnesene synthase gene (see for example http://www.sangamo.com/tech/tech.html.

Examples of post-transcription interventions include co-suppression or anti-sense strategies, a dominant negative approach, or techniques which involve ribozymes to digest, or otherwise be lethal to, RNA post-transcription of the target gene.

Co-suppression can be effected in a manner similar to that discussed, for example, by Napoli et al. Plant Cell 2, 279-290 (1990) and de Carvalho Niebel et al. Plant Cell 7, 347-358 (1995). In some cases, it can involve over-expression of the gene of interest through use of a constitutive promoter. It can also involve transformation of a plant with a non-coding region of the gene, such as an intron from the gene or 5' or 3' untranslated region (UTR).

Anti-sense strategies involve expression or transcription of an expression/transcription product capable of interfering with translation of mRNA transcribed from the target gene. This will normally be through the expression/transcription product hybridising to and forming a duplex with the target mRNA.

The expression/transcription product can be a relatively small molecule and still be capable of disrupting mRNA translation. However, the same result is achieved by expressing the whole polynucleotide in an anti-sense orientation such that the RNA produced by transcription of the anti-sense oriented gene is complementary to all or part of the endogenous target mRNA.

Anti-sense strategies are described generally by Robinson-Benion et al. Methods in Enzymol 254, 363-375 (1995) and Kawasaki et al., Artific. Organs 20, 836-845 (1996).

Genetic constructs designed for gene silencing may include an inverted repeat. An 'inverted repeat' is a sequence that is repeated where the second half of the repeat is in the complementary strand, e.g.,

```
5'-GATCTA . . . TAGATC-3'

3'-CTAGAT . . . ATCTAG-5'
```

The transcript formed may undergo complementary base pairing to form a hairpin structure provided there is a spacer of at least 3-5 bp between the repeated regions.

Another approach is to develop a small antisense RNA targeted to the transcript equivalent to an miRNA (Llave et al., Science 297, 2053-2056 (2002) that could be used to target gene silencing.

The ribozyme approach to regulation of polypeptide expression involves inserting appropriate sequences or subsequences (eg. DNA or RNA) in ribozyme constructs (McIntyre Transgenic Res. 5 257-262 (1996)). Ribozymes are synthetic RNA molecules that comprise a hybridizing region complementary to two regions, each of which comprises at least 5 contiguous nucleotides of a mRNA molecule encoded by one of the inventive polynucleotides. Ribozymes possess highly specific endonuclease activity, which autocatalytically cleaves the mRNA.

Also contemplated is the use of dicer technology (Stratagene)

Alternately, modulation may involve an increase in the expression and or activity of the polypeptide by over-expression of the corresponding polynucleotide, or by increasing the number of copies of the corresponding polynucleotide in the genome of the host.

As discussed in retention a gene silencing, approaches for over-expression may focus on the gene itself or on regulatory elements associated with the gene and which have an effect on expression of the encoded polypeptide. "Regulatory elements" is used here in the widest possible sense and includes other genes which interact with the gene of interest. Another approach is to modify transcription through expression of a naturally occurring and/or artificial transcription factor, for example an artificial zinc finger protein transcription factor designed to interact with the endogenous promoter of the alpha-farnesene synthase gene (see for example http://www.sangamo.com/tech/tech.html.

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain the necessary elements that permit transcribing the insert polynucleotide molecule, and, optionally, translating the transcript into a polypeptide. The insert polynucleotide molecule may be derived from the host cell, or may be derived from a different cell or organism and/or may be a recombinant polynucleotide. Once inside the host cell the genetic construct may become integrated in the host chromosomal DNA. The genetic construct may be lined to a vector.

To give effect to the above strategies, the invention also provides genetic constructs usually DNA constructs. The DNA constructs include the intended DNA (such as one or more copies of a polynucleotide sequence of the invention in a sense or anti-sense orientation or a polynucleotide encoding the appropriate ribozyme), preferably a promoter sequence and preferably a termination sequence (which control expression of the gene), operably linked to the DNA sequence to be transcribed. The promoter sequence is generally positioned at the 5' end of the DNA sequence to be transcribed, and is employed to initiate transcription of the DNA sequence. Promoter sequences are generally found in the 5' non-coding region of a gene but they may exist in introns (Luehrsen Mol. Gen. Genet 225, 81-93 (1991)) or in the coding region.

A variety of promoter sequences which may be usefully employed in the DNA constructs of the present invention are well known in the art. The promoter sequence, and also the termination sequence, may be endogenous to the target plant host or may be exogenous, provided the promoter and terminator are functional in the target host. For example, the promoter and termination sequences may be from other plant species, plant viruses, bacterial plasmids and the like. Preferably, promoter and termination sequences are those endogenously associated with the alpha-farnesene synthase genes.

Factors influencing the choice of promoter include the desired tissue specificity of the construct, and the timing of transcription and translation. For example, constitutive promoters, such as the 35S Cauliflower Mosaic Virus (CaMV 35S) promoter, will affect the transcription in all parts of the plant. Use of a tissue specific promoter will result in production of the desired sense or antisense RNA only in the tissue of interest. With DNA constructs employing inducible promoter sequences, the rate of RNA polymerase binding and initiation can be modulated by external stimuli, such as chemicals, light, heat, anaerobic stress, alteration in nutrient conditions and the like. Temporally regulated promoters can be employed to effect modulation of the rate of RNA polymerase binding and initiation at a specific time during development of a transformed cell. Preferably, the original promoters from the gene in question, or promoters from a specific tissue-targeted gene in the organism to be transformed are used. Other examples of promoters which may be usefully employed in the present invention include, mannopine synthase (mas), octopine synthase (ocs) and those reviewed by Chua et al. Science 244, 174-181 (1989).

The termination sequence, which is located 3' to the DNA sequence to be transcribed, may come from the same gene as the promoter sequence or may be from a different gene. Many termination sequences known in the art may be usefully employed in the present invention, such as the 3' end of the *Agrobacterium tumefaciens* nopaline synthase gene. However, preferred termination sequences are those from the original gene or from the target species to be transformed.

The DNA constructs of the present invention may also contain a selection marker that is effective in cells, to allow for the detection of transformed cells containing the construct. Such markers, which are well known in the art typically confer resistance to one or more toxins. One example of such a marker is the NPTII gene whose expression results in resistance to kanamycin or hygromycin, antibiotics which are usually toxic to plant cells at a moderate concentration. Alternatively, the presence of the desired construct in transformed cells can be determined by means of other techniques well known in the art, such as PCR or Southern blots.

Techniques for operatively linking the components of the inventive DNA constructs are well known in the art and include the use of synthetic linkers containing one or more restriction endonuclease sites. The DNA construct may be linked to a vector capable of replication in at least one system, for example, *E. coli*, whereby after each manipulation the resulting construct can be sequenced and the correctness of the manipulation determined.

The DNA constructs of the present invention may be used to transform a variety of plants including agricultural, ornamental and horticultural plants. In a preferred embodiment, the DNA constructs are employed to transform apple, banana, kiwifruit, tomato, cotton, rose, olive, potato, carnation, petunia, mango, papaya, lisianthus, chrysanthemum, rice, tea, hops and orchid plants.

As discussed above, transformation of a plant with a DNA construct including an open reading frame comprising a polynucleotide sequence of the invention wherein the open reading frame is orientated in a sense direction can, in some cases, lead to a decrease in expression of the polypeptide by co-suppression. Transformation of the plant with a DNA construct comprising an open reading frame or a non-coding (untranslated) region of a gene in an anti-sense orientation will lead to a decrease in the expression of the polypeptide in the transformed plant.

It will also be appreciated that transformation of other non-plant hosts is feasible, including well known prokaryotic and eukaryotic cells such as bacteria (e.g. *E. coli, Agrobacterium*), fungi, insect, and animal cells is anticipated. This would enable production of recombinant polypeptides of the invention or variants thereof. The use of cell free systems (e.g. Roche Rapid Translation System) for production of recombinant proteins is also anticipated (Zubay Annu Rev Genet 7, 267-287 (1973)).

The polypeptides of the invention produced in any such hosts may be isolated and purified from same using well known techniques. The polypeptides may be used in cell-free systems for enzymic synthesis of alpha-farnesene.

Techniques for stably incorporating DNA constructs into the genome of target plants are well known in the art and include *Agrobacterium tumefaciens* mediated introduction, electroporation, protoplast fusion, injection into reproductive organs, injection into immature embryos, high velocity projectile introduction, floral dipping and the like. The choice of technique will depend upon the target plant to be transformed.

Once the cells are transformed, cells having the DNA construct incorporated into their genome may be selected by means of a marker, such as the kanamycin resistance marker discussed above. Transgenic cells may then be cultured in an appropriate medium to regenerate whole plants, using techniques well known in the art. In the case of protoplasts, the cell wall is allowed to reform under appropriate osmotic conditions. In the case of seeds or embryos, an appropriate germination or callus initiation medium is employed. For explants, an appropriate regeneration medium is used.

In addition to methods described above, several methods are well known in the art for transferring DNA constructs into a wide variety of plant species, including gymnosperms angiosperms, monocots and dicots.

The resulting transformed plants may be reproduced sexually or asexually, using methods well known in the art, to give successive generations of transgenic plants.

The nucleotide sequence information provided herein will also be useful in programs for identifying nucleic acid variants from, for example, other organisms or tissues, particularly plants, and for pre-selecting plants with mutations in alpha-farnesene synthase or their equivalents which renders those plants useful. This provides for an accelerated breeding program to produce plants in which the content of alpha-farnesene and its derivatives is modulated. More particularly, the nucleotide sequence information provided herein may be used to design probes and primers for probing or amplification of alpha-farnesene synthase. An oligonucleotide for use in probing or PCR may be about 30 or fewer nucleotides in length. Generally, specific primers are upwards of 14 nucleotides in length. For optimum specificity and cost effectiveness, primers of 16-24 nucleotides in length are preferred. Those skilled in the art are well versed in the design of primers for use in processes such as PCR.

If required, probing can be done with entire restriction fragments of the gene disclosed herein. Naturally, sequences based upon FIG. 4 or the complements thereof can be used. Such probes and primers also form aspects of the present invention.

Methods to find variants of the of polynucleotides of the invention from any species, using the sequence information provided by the invention, include but are not limited to, screening of cDNA libraries, RT-PCR, screening of genomic libraries and computer aided searching of EST, cDNA and genomic databases. Such methods are well known to those skilled in the art.

The invention will now be illustrated with reference to the following non-limiting Examples.

EXAMPLES

The following Examples further illustrate practice of the invention.

Example I

Identification of the Alpha-farnesene Synthase Gene

Plant material and GC-MS analysis: Tree-ripened 150 DAFB apples (*Malus domestica*) were harvested from Royal Gala trees grown in a HortResearch orchard at Hawkes Bay, New Zealand. Twelve fruit were selected for analysis and were placed into a 5 L wide-necked round-bottomed sampling vessel with a ground glass flat flange joint. The vessel was covered with a glass lid with a sealed ground glass joint inlet socket containing a gas line and a volatile sorbent cartridge containing 100 mg Chromosorb 105. The headspace in the flask was allowed to equilibrate at 23° C. for 1 hour, after which the headspace was purged with $N_2(g)$ at 25.0 ml/min while being trapped for 15 min. The Chromosorb cartridge was dried with a $N_2(g)$ flow at 10 psi, 35 C for 15 min prior to analysis. The volatiles were thermally desorbed from the Chromosorb traps for 3 min at 150° C. into the injection port of the gas chromatograph (GC) HP5890. The GC system was equipped with a DB-Wax capillary column (J & W Scientific, Folsom, USA), 30 m×0.32 mm i.d., with a 0.5 µM film thickness. The carrier gas was helium at a flow rate of 30 cm/sec. The GC oven was programmed to remain at 30° C. for 6 min, then to increase by 3° C./min to 102° C., followed by an increase of 5° C./min to 190° C., which was maintained for 5 min. The column outlet was split to a mass spectrometer (VG70SE), in addition to the GC's flame ionisation detector (GC-FID/MS). The mass spectrometer operated in electron impact ionisation (EI-MS) mode at 70 eV with a scan range 30-320 amu. Component identification was assisted with mass spectra of authentic standards, library spectra (NIST and in-house) and GC retention indices. Quantitative data was obtained by measuring the sample peak areas relative to an authentic standard.

Isolation of mRNA and cDNA library construction: The skin of the 150 DAFB apples was removed with a peeler and total RNA was extracted from the peeled skin by an adaptation of the method of Gomez and Gomez (Langenkamper, et al., Plant Mol. Biol. 36, 857-869 (1998)). mRNA purified from the total RNA by oligo(dT)-cellulose chromatography (Pharmacia) was used to construct a Lambda ZAP-CMV (Stratagene) cDNA library according to the manufacturer's instructions. The cDNA-containing pBK-CMV plasmids were massed excised and used to transform *E. coli* XLOLR (Stratagene). The plasmids were isolated from the XLOLR colonies and partially sequenced. All sequences on the database were BLASTed against the NRBD90 database (Altschul, et al., Nucleic Acids Res. 25, 3389-3402 (1997).) and putative terpene synthase cDNA sequences were identified by their similarity to known terpene synthases based on key motifs. A full-length terpene synthase sequence (EST57400) was identified and its polynucleotide sequence determined.

Cloning into pET-30: For functional expression, a cDNA fragment encoding EST57400 was excised from pBK-CMV57400 using a EcoRI restriction endonuclease site immediately adjacent to the start ATG and the vector XhoI restriction site. The resultant 1899 bp cDNA sequence was then subcloned in frame into the expression vector pET-30a (Novagen), which was also digested with EcoRI and XhoI, yielding plasmid pET-30a57400. Plasmid pET-30a57400 was then transformed into *E. coli* BL21-CodonPlus™-RIL cells (Stratagene). The clone was resequenced at the 5' end to ensure the inserted cDNA was in frame.

Expression and characterization of alpha-farnesene synthase from bacterial cultures: *E. coli* BL21-Plus™-RIL cells harbouring pET-30a57400, and empty pET-30 vector as a control, were grown overnight at 37° C. in Lauria-Bertani media supplemented with 30 µg/ml kanamycin and 50 µg/ml chloramphenicol. A 500 µl aliquot of overnight culture was used to inoculate 50 ml of fresh 2×YT medium supplemented with 30 µg/ml kanamycin and 50 µg/ml chloramphenicol. The culture was grown at 37° C. with vigorous agitation to $A_{600}$=0.6 before induction with 0.3 mM isopropyl-β-D-thiogalactopyranoside (IPTG) and simultaneous addition of farnesyl diphosphate (FDP) (10 µM). The culture was immediately transferred to a 30° C. incubator, or 16 or 37° C. incubators depending on the experiment.

Headspace analysis of bacterial cultures: The headspace in the vessels above the bacterial cultures was collected immediately after the addition of FDP using solid phase micro extraction (SPME). The SPME fibres (65 µm PDMS/DVB, Supelco, Australia) were conditioned for 45 min at 260° C. and the background analysed for contamination using GC-FID (HP5890) prior to use. The headspace volatiles were collected for 4 hours at 30° C. with continuous agitation (110 rpm). Prior to analysis using a GC-FID/MS, the fibres were stored at ambient temperature in septum sealed glass vials. The volatiles were desorbed from the fibres for 5 minutes at 250° C. in the GC injection port. The GC system was equipped with a DB-Wax capillary column (J & W Scientific, Folsom, USA), 30 m×0.25 mm i.d., with a 0.5 µm film thickness. The carrier gas was helium at a flow rate of 30 cm/sec. The GC oven was programmed to remain at 30° C. for 6 min, then to increase by 3° C./min to 102° C., followed by an increase of 5° C./min to 210° C., which was maintained for 11 min. The mass spectrometer operated in electron impact ionisation (EI-MS) mode at 70 eV with a scan range of 30-320 amu. Peak identification was carried out by comparison of sample spectra with those from NIST, Wiley, and our own mass spectra libraries and confirmed by retention indices of authentic standards and literature values (Davies, J. Chrom. 503, 1-24, (1990)). Quantitative data was obtained by measuring sample peak area relative to an internal standard, hexadecane, which had been added to the cultures at the same time as the FDP.

Expression time course for induced and non-induced cultures: 6×50 ml bacterial cultures harbouring pET-30a57400 were prepared as above. At $A_{600}$=0.6 three of the cultures were induced with 0.3 mM IPTG leaving the remaining cultures non-induced. Cultures were then incubated for one, three or five hours at 30° C. and the headspace volatiles were collected as described above.

Characterization of alpha-farnesene synthase from bacterial extracts and partially purified alpha-farnesene synthase recombinant protein: Cultures were set up, grown and induced as above. Following induction, cultures were immediately transferred to a 24° C. incubator and allowed to grow for a further 18-20 hours with continuous agitation and then cells harvested by centrifugation (2000×g for 10 min). Pelleted cells were resuspended in either 20 ml binding buffer (5 mM imidazole, 0.5 mM NaCl, 10 mM DTT, 20 mM Tris-HCl (pH 7.9) or 20 ml extraction buffer (25 mM MOPS (pH 7.0), 10 mM sodium ascorbate, 25 mM KCl, 10 mM DTT, 10% glycerol). Cells were disrupted with 2× exposure to 12,700 psi in a French Pressure Cell Press (American Instrument Co. Inc, Silver Spring, Md. USA) and then centrifuged at 8000×g for 15 min. 5 ml of supernatant was transferred to a 50 ml test-tube and adjusted to 10 mM $MgCl_2$ and 20 μM $MnCl_2$. FDP (100 μM) was added and the reaction mixture was incubated at 30° C. Headspace volatiles were collected as in the same manner as whole cultures. The remainder of the extract (15 ml) was applied to PD-10 gel filtration columns (Amersham-Pharmacia Biotech) pre-equilibrated with either binding or extraction buffer (DTT omitted). Eluent fractions were then pooled and purification of recombinant protein was carried out in a single step using immobilised metal affinity chromatography (IMAC). The eluent was applied to a Hi-Trap Chelating HP column (Amersham-Pharmacia Biotech) charged with $Ni^+$. Non bound proteins were removed and recombinant protein was eluted following the manufacturer's specifications. Five ml samples of the eluted protein were transferred to 50 ml test-tubes and adjusted to 10 mM $MgCl_2$, 20 μM $MnCl_2$ and 10 μM FDP was added. Headspace volatiles were collected as in the bacterial cultures. Aliquots of the remaining recombinant protein were stored at −80° C. in 20% glycerol until required.

Electrophoresis and Western analysis: Whole culture, French Press His-purified and non His-purified protein extracts were analysed by SDS-PAGE, using 10% polyacrylamide gels. Protein bands were either visualised using Colloidal Coomassie or were transferred on to Immobilin-P PVDF membrane (Millipore). Blotted proteins were incubated with Anti-$His_6$ monoclonal (Roche) primary and Anti-Mouse IgG-AP (Stressgen) secondary antibodies and were detected using 1-STEP™ NBT/BCIP (Pierce) alkaline phosphatase detection reagent.

Protein quantification: Protein concentrations of extracts and partially purified recombinant proteins were determined according to Bradford using the Biorad kit according to manufacturers specification using a Spectromax Plus spectrophotometer, using bovine serum albumin (BSA) as the standard.

Results

Headspace analysis of volatiles emitted from 150 DAFB apples: It is well established that alpha-farnesene is synthesised in apple skin tissue and detected in headspace analyses. Typically two isomers of alpha-farnesene are found in apple skin, (E,E) and (Z,E) alpha-farnesene (Matich, et al., Anal. Chem. 68, 4114-4118 (1996), Bengtsson, et al., J. Agric. Food Chem. 49, 3736-3741 (2001)). These two isomers are usually identified in the ratio of 100:1 respectively (Matich, et al., Anal. Chem. 68, 4114-4118 (1996)). In the headspace of the 150 DAFB apples analysed only the 'all trans' (E,E) isomer of alpha-farnesene was identified (FIG. 5). This isomer was present at low levels, on average 4 ng (E,E) alpha-farnesene per fruit. The (E,E) alpha-farnesene isomer had a retention time of 42.57 minutes that was used to calculate the Kovats retention index for this compound. The retention index and the mass spectra positively identified this compound as (E,E) alpha-farnesene.

Sequence analysis of alpha-farnesene synthase: Sequencing of the cDNA in pBK-CMV that encoded alpha-farnesene synthase revealed an insert size of 1926 base pairs excluding the poly(A) tail (FIG. 3, SEQ ID NO:1). The cDNA sequence had a predicted ORF of 576 amino acids beginning with a putative start methionine 61 bases in from the 5' end (FIG. 4, SEQ ID NO:2). The molecular mass of alpha-farnesene synthase is predicted to be 66 kD. The predicted amino acid sequence of alpha-farnesene synthase does not have a chloroplast-signalling peptide sequence (Emanuelsson, et al., 300, 1005-1016 (2000)), which is typical of monoterpene and diterpene synthases. As has been found for all other terpene synthases the predicted amino acid sequence of alpha-farnesene synthase contains a DDXX(D, E) motif (DDVYD) at amino acids 326 to 330 that is involved in the binding of the metal ions necessary for catalysis. alpha-farnesene synthase was not shown to contain the angiosperm sesquiterpene consensus sequence GVYXEP (Cai et al Phytochem 61, 523-529 (2002)), instead containing a highly similar GVAFEP motif from amino acids 301 to 306. It was also shown to contain the $RRX_8W$ motif at amino acids 33 to 43, which is a common characteristic of Tps-d and Tps-b monoterpene synthases. (Duderava, N., Martin, D., Kish, C. M., Kolosova, N., Gorenstein, N., Fäldt, J., Miller, B., and Bohlmann, J. (2003) Plant Cell. 15, 1227-1241.)

Bohlmann, Meyer-Gauen and Croteau (Proc. Natl. Acad. Sci. USA 95, 4126-4133 (1998)) compared the amino acid sequences of 33 terpene synthases and showed that there were seven absolutely conserved amino acid residues. Alpha-farnesene synthase contains six of these seven absolutely conserved amino acids. They also found that six positions were absolutely conserved for aromatic amino acids and four positions were absolutely conserved for acidic amino acids. In alpha-farnesene synthase, four of the six aromatic positions and all of the four acidic positions are conserved.

The predicted amino acid sequence for alpha-farnesene synthase (a sesquiterpene synthase) most closely resembles the amino acid sequences of a putative monoterpene from *Cinnamomum tenuipilum* (Zeng et al, Genbank CAD29734, 2002), having 39.8% identity and 56.3% similarity from the predicted amino acids 34 to 574. A putative monoterpene synthase from *Melaleuca alternifolia* (tea tree) (Shelton et al, Genebank AAP40638, 2003) has the second highest similarity, with 38.7% identity and 54.1% similarity from the predicted amino acids 34 to 574 and a putative monoterpene synthase from *Quercus ilex* (holly oak) (Fischbach, Genbank CAC41012, 2001), having 37.9% identity and 55.8% similarity from the predicted amino acids 34 to 574.

The nucleic acid sequences of the alpha-farnesene synthase show homology to very short stretches of the mRNA of a few sesquiterpene synthases. One area of homology lies between nucleotides 918 and 946. For example, cadinene synthase from *Gossypium arboreum* (tree cotton) (Chen, Wang, Chen, Davisson and Heinstein, 1996) has 24 out 25 identical bases in the region between nucleotides 918 and 946 and a putative sesquiterpene synthase from *Artemisia annua* has 25 out 26 bases identical in this region (Van Geldre et al., Plant Sci. 158, 163-171 (2000)). Between nucleotides 367 and 386, E- a-bisabolene synthase of *Abies grandis* (grand fir) has 20 out of 20 identical bases.

The predicted isoelectric point for alpha-farnesene synthase synthase is 5.1 which is similar to the isoelectric point calculated for other sesquiterpene synthases. For example, two sesquiterpene synthases isolated from *Artemisia annua*, cASC34 and cASC125, have isoelectric points of 5.28 and 5.50, respectively (Van Geldre et al., Plant Sci. 158, 163-171 (2000)).

The cDNA sequence for alpha-farnesene synthase (EST 57400) was obtained from a cDNA library constructed from Royal Gala 150 DAFB apple skin. Three other truncated cDNAs with polynucleotides across the sequenced 5' end identical to EST 57400 were also isolated. One was from Royal Gala 126 DAFB fruit cortex, one from Royal Gala floral buds, and the third truncated one from Pinkie leaf. Another truncated cDNA obtained from Aotea leaf had seven base pair differences out the 675 bases sequenced, resulting in 5 amino acid changes Western analysis: Western analysis confirmed the presence of a soluble expression product within the expected size range (65-75 kDa His tag inclusive) for alpha-farnesene synthase in both the French Press extracts and partially purified recombinant protein extracts. No similar-sized band was detected in either the pET-30a control purified or non-purified extracts.

Characterisation of alpha-farnesene synthase (E,E)-alpha-farnesene and small amounts (Z,E)-alpha-farnesene were detected in the headspace of bacterial cultures and extracts harbouring pET-30a57400. Controls comprising *E. coli* BL21 cells transformed with pET-30a lacking the alpha-farnesene synthase cDNA insert gave negligible or no alpha-farnesene. (E,E)-alpha-farnesene production in both cultures and crude extracts, although not dependent on precursor addition, was shown to be dependent on the presence of the alpha-farnesene synthase cDNA insert. Although a peak was found at a similar retention time in the control as the alpha-farnesene (42.24 min), the mass spectra showed this to be citral. Addition of GDP to bacterial cultures did not produce either alpha-farnesene or any monoterpenes.

Figure 6:
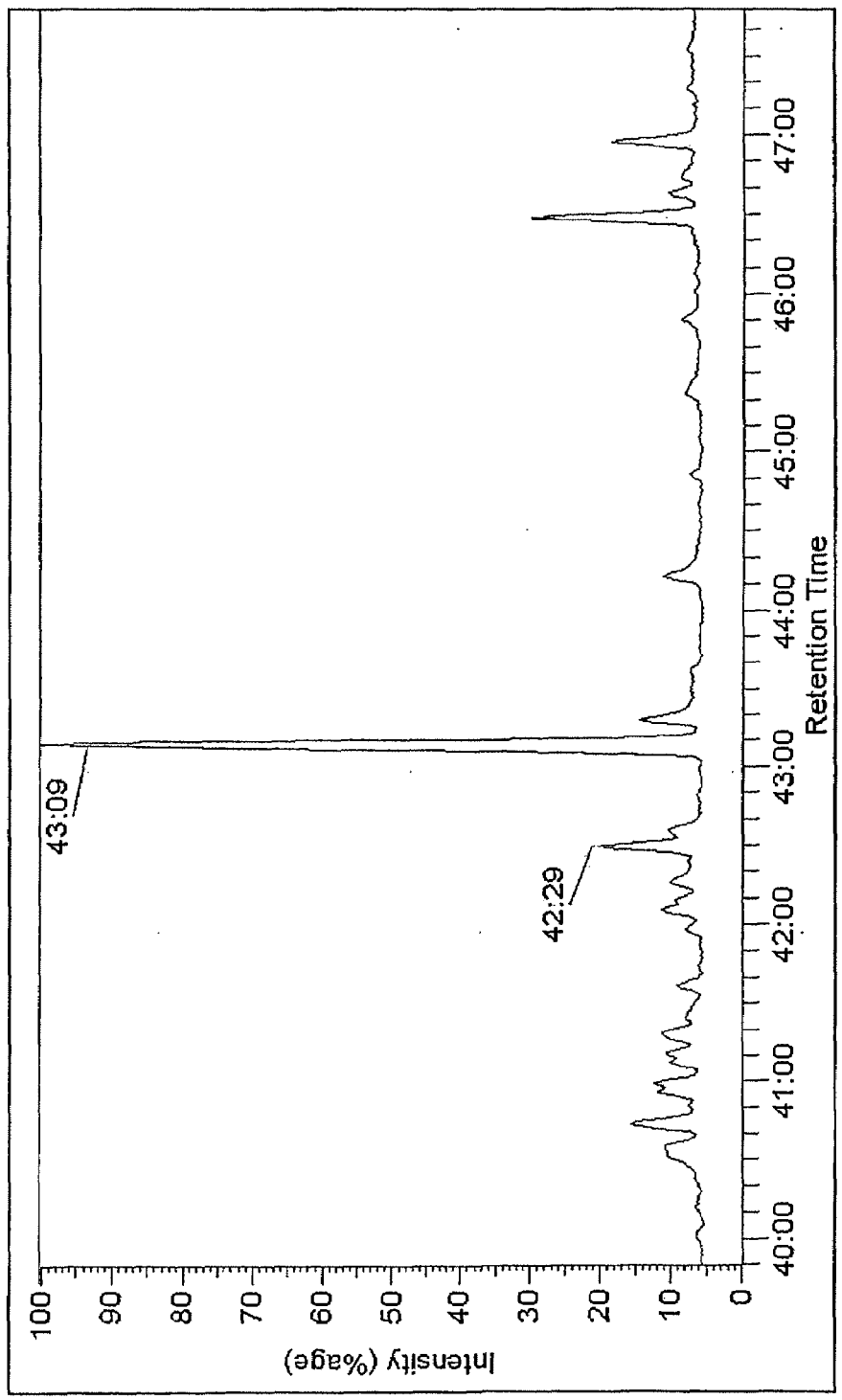
FIG. 6 shows a GC-MS trace of headspace above nickel purified cell free extracts (in binding buffer) harbouring alpha-farnesene synthase cDNA showing (E,E) alpha-farnesene (retention time 43.09 minutes) and (Z,E) alpha-farnesene (retention time 42.29 minutes).

Headspace analysis of partially purified recombinant enzyme, whether derived from extraction in His purification binding buffer or sesquiterpene extraction buffer, showed (E,E)-alpha-farnesene as the major product with minor amounts of (Z,E)-alpha-farnesene present (FIG. 6). This required added FDP, no alpha-farnesene was produced without the added precursor. Purified enzyme that had been stored in glycerol for 4 weeks at −80 C was reassayed with only 15% loss of activity.

The bacterial cultures and crude extracts harbouring the alpha-farnesene cDNA showed leaky expression under non-inducing conditions. However volatile trapping over a 5 hour period demonstrated that addition of IPTG increased the production of both isomers relative to the samples that were not induced.

EST 57400 therefore encodes an alpha-farnesene synthase that makes only alpha-farnesene.

Example II

Properties of the Enzyme

Figure 7:
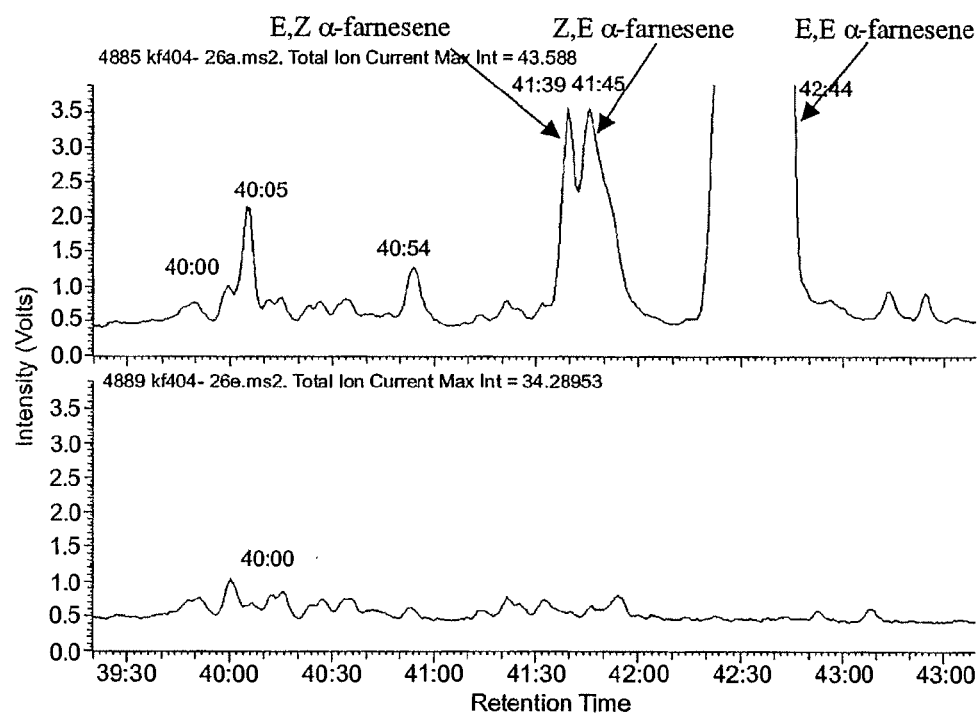
FIG. 7 shows isomeric forms of alpha-farnesene produced in vitro by purified recombinant alpha-farnesene synthase in response to feeding a precursor FDP of mixed isomers.

Isomer Specificity: FDP precursor consisted of a mixture of E,E and E,Z forms in most experiments and analyses indicated that both E,E and Z,E isomers of alpha-farnesene were produced by the gene alpha-farnesene synthase. To test isomer specificity we fed FDP precursor in the ratios 41.3% E,E isomer, 28.7% E,Z isomer, 24.7% Z,E and 5.4% Z,Z to purified protein extracts in a standard in vitro activity experiment. Following 2 h trapping with SPME fibres as earlier described three of the four isomers of alpha-farnesene were produced (see FIG. 7). The peak at 40.54 may be Z,Z alpha-farnesene but it has not been confirmed. These results indicate the enzyme has no isomeric specificity and will produce alpha-farnesene isomers dependent on the isomeric form of the FDP precursor.

Optimisation of large-scale production of protein: *E. coli* BL21-Plus™ -RIL cells harbouring pET-30a57400 were grown overnight at 37° C. in Lauria-Bertani media supplemented with 30 µg ml$^{-1}$ kanamycin and 50 µg ml chloramphenicol$^{-1}$. 5 mL aliquots of overnight culture were used to inoculate 4×300 mL of fresh 2×YT medium supplemented with 30 µg ml$^{-1}$ kanamycin and 50 µg ml$^{-1}$ chloramphenicol in 1 L baffled flasks. Cultures were grown at 37° C. with vigorous agitation to $A_{600}$=0.8, then removed to 4° C. to equilibrate to 16° C. before induction with 0.3 mM IPTG. Induced cultures were then incubated at 16° C. and 220 rpm for a further 50 hours. Cells were pelleted by centrifugation (2500×g; 10 min) and stored overnight at −20° C. The following day cell pellets were resuspended in 15 mL His6 binding buffer and cells were disrupted by 3 passes through an EmulsiFlex®-C15 high-pressure homogeniser (Avestin) with a pressure setting between 15000-20000 psi. Cell debris was pelleted by centrifugation 2× at 10000×g for 15 min; 4° C. (Sorval SS34 rotor). The supernatant was filtered through a 0.45 µm filter (Amicon). Filtered extract was desalted and passed over a Nickel affinity column, followed by passage through a 30 kDa filter (Millipore).

Protein concentration was determined from the extinction coefficient (VectorNTI version 8) and the purified extract adjusted to ~1 mg protein/mL with His6 elution buffer containing 10% glycerol and 1 mM DTT. The extract was then separated into 100 µl aliquots and stored at −80° C. until required.

Protein oligomerisation: Approximately 500 µg of purified protein was loaded onto a 600×16 mm S300 Sephacryl column (Pharmacia) at a flow rate of 1 mL min$^{-1}$. The column was preequilibrated and eluted with 50 mM Bis-tris propane buffer containing 10% glycerol with either 50 mM KCl or 0.5 M KCl with or without 7 mM MgCl$_2$. Fractions corresponding to protein peaks were assayed after adjusting to 7 mM MgCl$_2$ for activity after addition of 25 µM $^3$H-FDP. Molecular mass of active fractions was calculated based on comparison to standards of known molecular mass.

Figure 8:
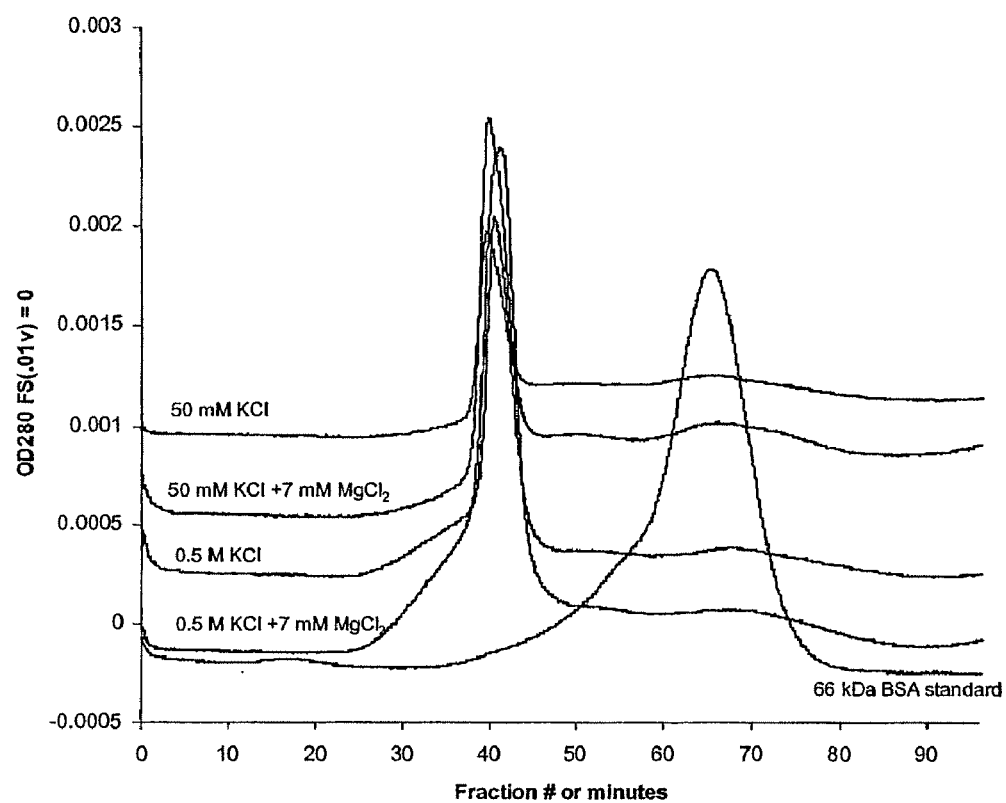
FIG. 8 shows the protein elution profile and approximate molecular mass of alpha-farnesene synthase on Sephacryl S-300 HR Gel filtration chromatography.
Figure 9:
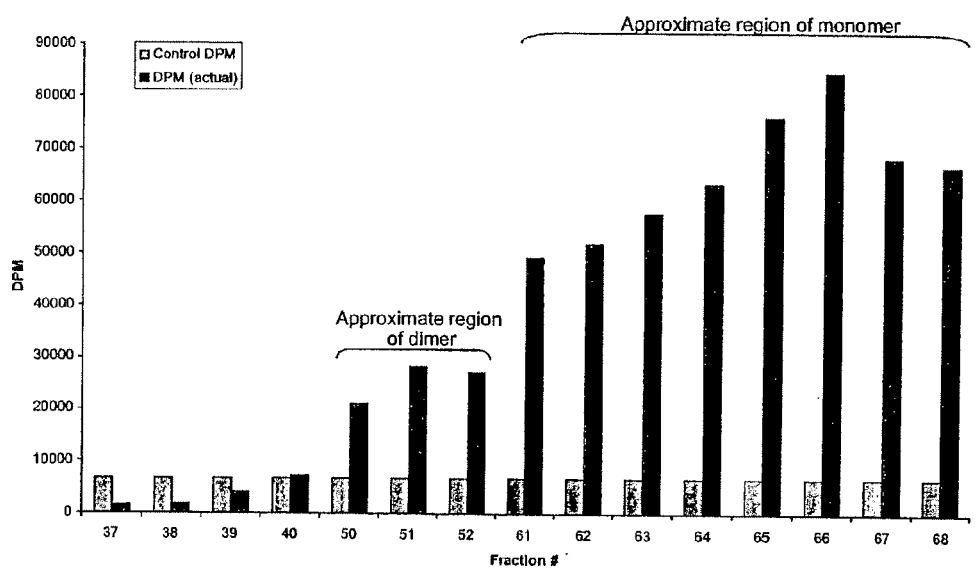
FIG. 9 shows alpha-farnesene synthase activity of fractions of purified protein after application to S-Sephacryl 300 HR Gel Filtration.

Results: The alpha-farnesene synthase protein acts primarily as a monomer (see FIGS. 8 and 9). While the data suggests a small amount of activity could be due to oligomeric forms, over 70% of the activity is due to monomeric enzyme. FIG. 8 shows the protein elution profile and approximate molecular mass of alpha-farnesene synthase on Sephacryl S-300 HR Gel filtration chromatography. Four different purified extracts were compared with contrasting salt and Mg profiles. The major peak at fraction 40 is not alpha-farnesene synthase, shows almost no protein on an SDS gel and is likely to be predominantly DNA; enzymatic activity centers on fractions between 60 and 70 (see FIG. 9).

Kinetic Studies: For kinetic studies, alpha-farnesene synthase active protein that had been induced in culture and purified as described for protein optimisation was added to a minimal assay buffer containing 50 mM Bis-Tris-Propane (pH 7.5), 10% (v/v) glycerol, 1 mM DTT and 0.1% (v/v) Tween-20. Radioactive FDP was added variously depending on the experiment. One mL assays containing 1-2 µg of protein were overlaid with 0.6 mL pentane and incubated in 1.5 mL microfuge tubes for 2 hours at 30° C. and 150 rpm. All assays were performed in triplicate. Following incubation assays were immediately placed on ice and a 200 µL aliquot of the pentane layer removed for analysis. The aliquots were added to 1.5 mL microfuge tubes containing 0.7 DL Organic Counting Scintillant (OCS) (Amersham) and vortexed briefly. Scintillation analysis was performed using a Wallac 1409 Liquid Scintillation Counter ($^3$H efficiency≈70%).

Kinetic studies with $^3$H-FDP (10.06 Mbq/mL) as substrate (concentration range 1 µm to 100 µM with saturating Mg$^{2+}$ and Mn$^{2+}$) were carried out to determine Km for FDP. Kinetic constants for Mg$^{2+}$, and Mn$^{2+}$ at 25 µM $^3$H-FDP (assay range 25 µM to 25 mM and 1 µM to 1 mM of the chloride salts respectively) were determined. The effect on enzyme activity of metal co-factors with and without salts was also tested. Mg$^{2+}$ and Mn$^{2+}$ were added in the presence and absence of 50 mM KCL and 50 mM NaCl in all possible combinations. Controls included incubation without enzyme, with enzyme but without metal ion cofactors and with enzyme and cofactors in the presence of 10 mM EDTA.

For determination of the enzyme pH optimum, assays were carried in a tri-buffer system containing 51 mM diethanolamine, 100 mM MES, and 51 mM N-ethylmorpholine at pH values between 4.5 and 9.6 with 7 mM Mg, 150 µM Mn and 25 µM FDP, 10% (v/v) glycerol, 1 mM DTT and 0.1% (v/v) Tween-20. Optimal temperatures for enzyme activity in the range 18° C.-50° C. were also determined using the standard assay buffer and 7 mM Mg, 150 µM Mn and 25 µM FDP. Kinetic constants were determined from the DPM data by nonlinear regression using the Origin50 graphics package. Data presented represents the means of three determinations with standard errors within ±10% and with background DPM calculated from controls subtracted. All experiments were carried out at least twice.

Figure 10:
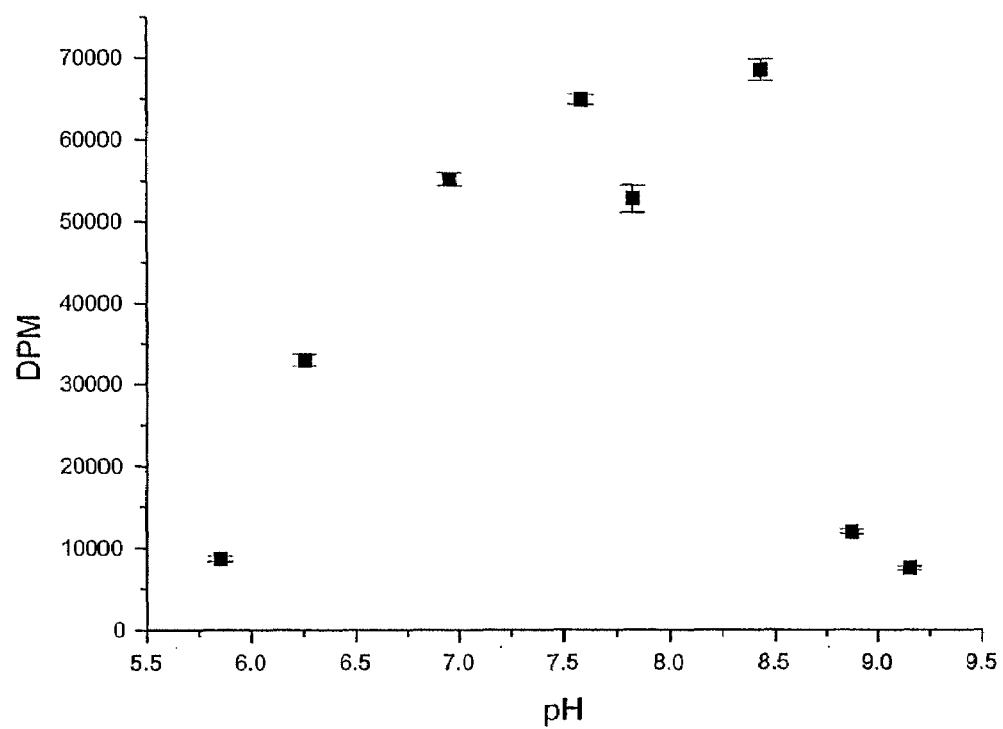
FIG. 10 shows the optimum pH for alpha-farnesene synthase activity. Data are means plus SE of means based on 3 replicates per experiment. Assay conditions include saturating $Mg^{++}/Mn^{++}$ (7 mM/150 µM) at pH 7.5.

Results: pH alpha-farnesene synthase showed a broad pH optimum between pH7 and 8.5 (FIG. 10). Repeated experiments indicated a slight reduction in activity at ~pH7.8. There was no difference in product produced over the optimal pH range for activity (data not shown). This pH range is similar to that (between pH 7 and 9)reported for other characterised sesquiterpene synthases in the literature (Cai et al Phytochemistry 61, 523-529 (2002); Steele et al J. Biol. Chem. 273, 2078-2089 (1998))

Figure 11:
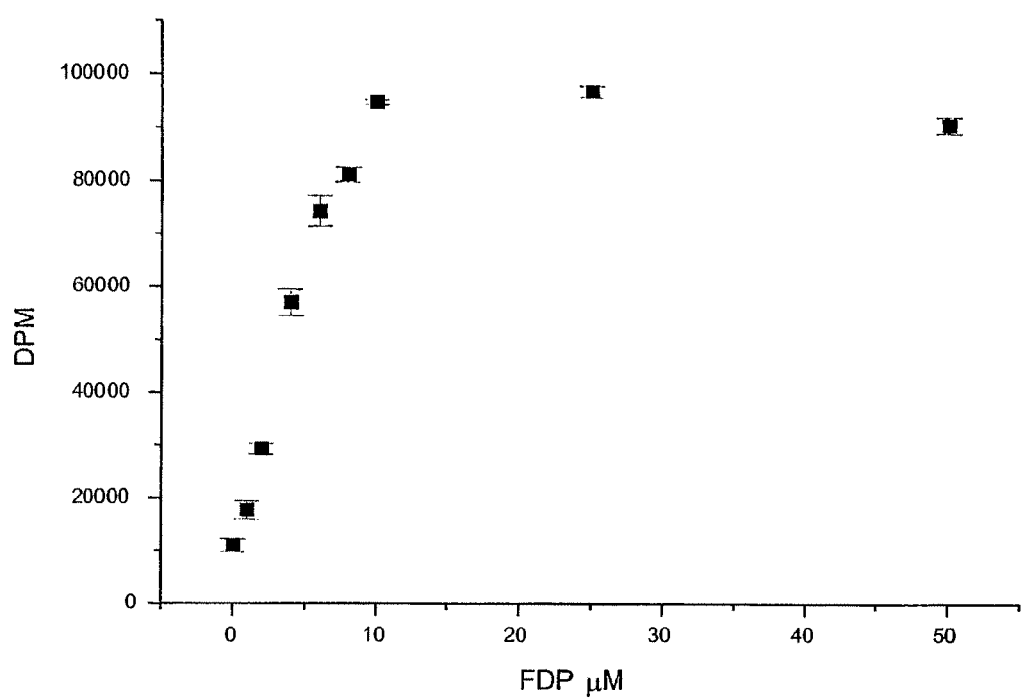
FIG. 11 shows effect of increasing concentrations of FDP on alpha-farnesene synthase activity in the presence of saturating metal ions. Assay conditions include saturating FDP (25 µM) and saturating $Mg^{++}/Mn^{++}$ (7 mM/150 µM).
Figure 12:
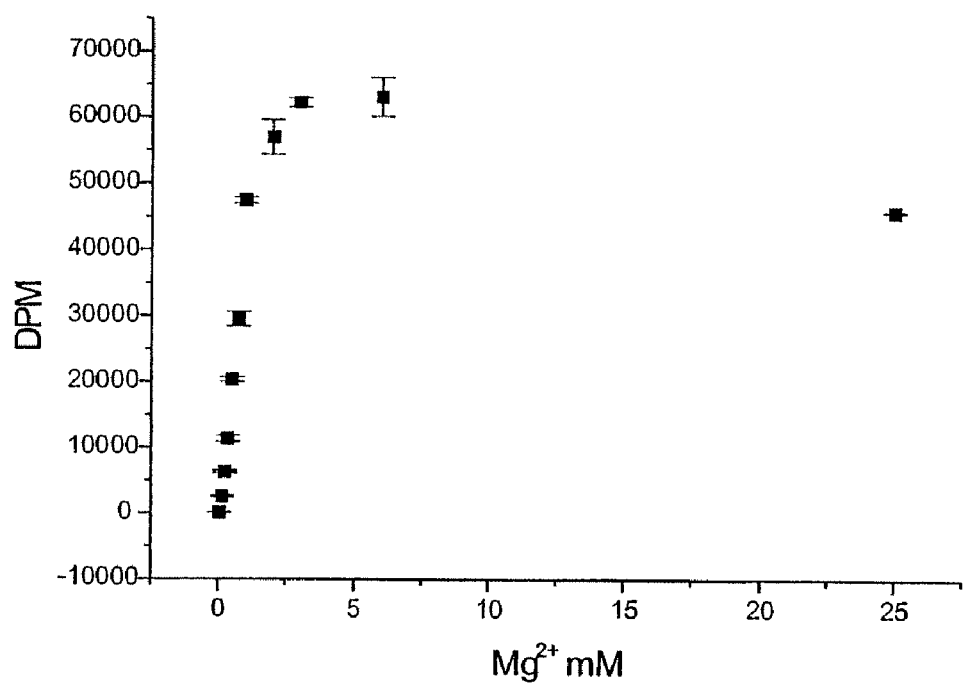
FIG. 12 shows effect of $Mg^{2+}$ on activity of alpha-farnesene synthase with saturating FDP (25 µM).
Figure 13:
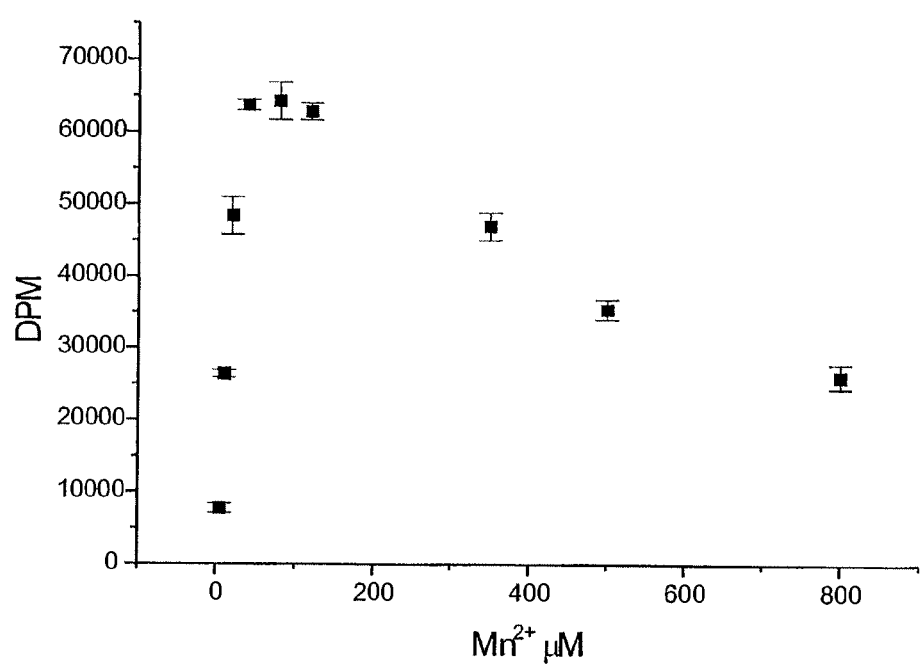
FIG. 13 shows effect of $Mn^{2+}$ on activity of alpha-farnesene synthase with saturating FDP (25 µM). Data are means and SE of three replicates from 1 experiment.

Km The Km for FDP was between 2.5 and 3.5 µM (FIG. 11) with saturating concentrations at 12 µM. No precursor inhibition was found at concentrations of FDP up to 50 µM. Km for the cofactor $Mg^{2+}$ was between 600 and 800 µM (FIG. 12) with a slight inhibition (23%) of activity with high (25 mM) concentrations; and the Km for $Mn^{2+}$ was between 10 and 20 µM with at least 50% inhibition of activity at high (>800 µM) concentrations (FIG. 13). Reported Kms in the literature range from 0.4-4.5 µM for FDP, 70-150 µM for Mg, 7-30 µM for Mn for other sesquiterpene synthases (eg Cai et al Phytochemistry 61, 523-529 (2002), Steele et al J. Biol. Chem. 273, 2078-2089(1998)).

Other metal ion effects Activity of alpha-farnesene synthase was enhanced with addition of $K^+$ ions (Table 1). Addition of $Na^+$ ions resulted in a slight non significant enhancement of activity, indicating the enhancement was due to the form of metal ion and not a general salt response.

TABLE 1

Relative activity of alpha-farnesene synthase due to additions of metal ions in the presence of saturating FDP.

| Metal ion | $V_{rel}$ (%) |
|---|---|
| Mg/KCl (7 mM/50 mM) | 100 |
| Mn/KCl (150 µM/50 mM) | 41 |
| Mg/Mn/KCl (7 mM/150 µM/50 mM) | 69 |
| Mg (7 mM) | 16 |
| Mn (150 µM) | 13 |
| Mg/Mn (7 mM/150 µM) | 18 |
| Mg/NaCl (7 mM/50 mM) | 23 |
| Mn/NaCl (150 µM/50 mM) | 15 |
| Mg/Mn/NaCl (7 mM/150 µM 50 mM) | 24 |

Figure 14:
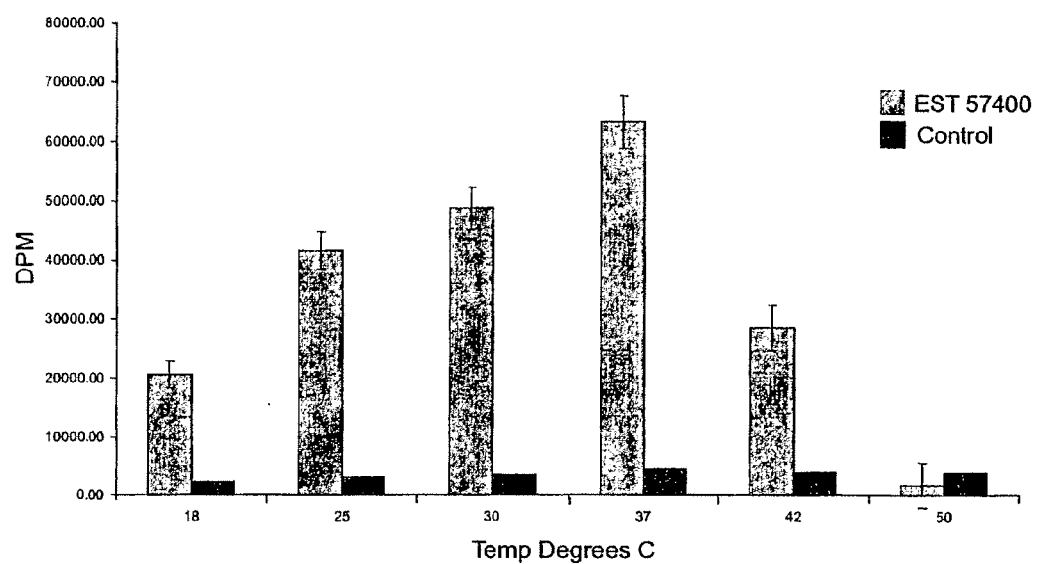
FIG. 14 shows the activity of alpha-farnesene synthase at different temperatures measured with saturating FDP (25 µM) and metal cofactors $Mg^{++}/Mn^{++}$ (7 mM/150 µM).

Temperature Maximum alpha-farnesene synthase activity occurred at 37° C., with a sharp reduction in activity at higher temperatures (FIG. 14). Activity was not detectable at 50° C., whereas at low temperatures (13° C.) enzyme activity remained although reduced by two thirds. This is similar to that reported for other sesquiterpene synthases.

Storage
Protein stored at −80° C. for 9 months lost activity (92.5% loss). This stored protein also showed a decrease in Km for FDP to ~1.5 µM. However Km for Mg, Mn and the pH response were unchanged.

Example III

Expression in Plants

Transient expression in *Nicotiana benthamiana* leaves: Transformation of *N. benthamiana* leaves was performed according to Hawes et al. (Hawes, C., Boevink, P., and Moore, I., GFP in plants, in Fluorescence microscopy of proteins: a practical approach., V. Allen, Editor. 1999, Oxford University Press: Oxford. p. 163-177 (2000)). *Agrobacterium tumefaciens* strain GV3101 (MP90) containing pHEX2 binary vector harbouring EST 57400, and P19 vector expressing a viral suppressor of mRNA silencing (Voinnet et al. Plant J 33, 949-956 (2003)) as a control were grown in 5 ml cultures of 2YT media containing rifampicin (10 mg ml$^{-1}$); gentamycin (25 mg ml$^{-1}$); and spectinomycin (100 mg ml$^{-1}$) for 24 hours at 28° C. The cells were collected by centrifugation (3,500×g; 10 minutes), and resuspended in infiltration medium (50 mM MES pH5.6, 0.5% (w/v) glucose, 2 mM $Na_3PO_4$, 100 mM acetosyringone (made freshly from 200 mM acetosyringone/DMSO stock)) to a final $OD_{600}$ of 0.5-0.6. The bacterial suspension was injected through the stomata on the underside of detached *N. benthamiana* leaves, using a 1 ml syringe with no needle attached. The infiltrated area on the leaf was marked with an indelible marker pen for later identification. Plants with infected leaves were grown for 7 days under standard green house conditions.

Transformed *N. benthamiana* leaves and control leaves were infiltrated with distilled water containing 25 µM FDP, 7 mM $MgCl_2$ and 50 mM KCl. One hour later, 3 leaves per treatment were excised and placed in 50 mL glass test tubes and the headspace above the leaf tissue was collected using solid phase micro extraction (SPME) for 12 hours at 30° C. The experiment was repeated without preinfiltration. The complete experiment was carried out on two occasions with independently transformed plants.

Figure 15:
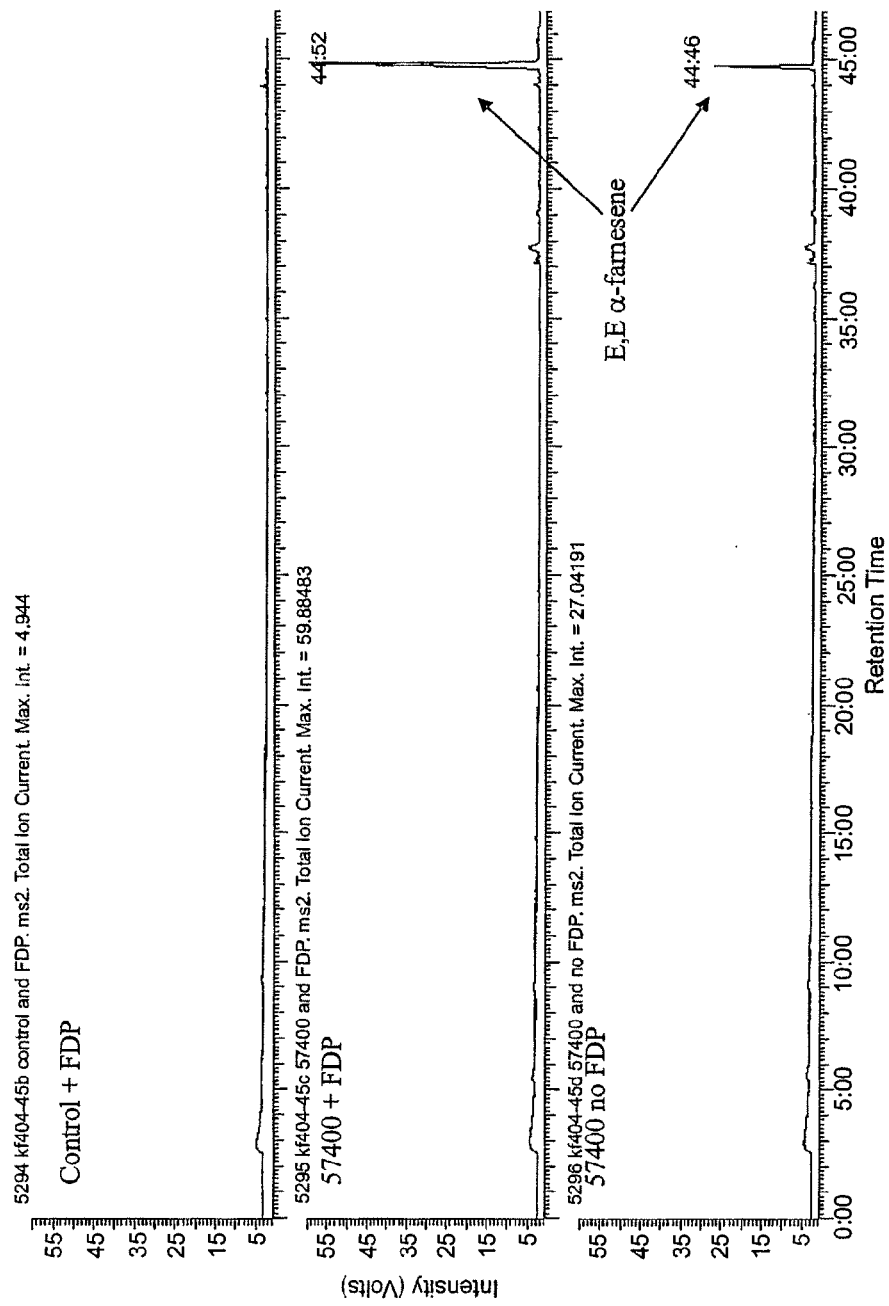
FIG. 15 shows an example of one experiment showing production of E,E alpha-farnesene in N. benthamiana leaves, with and without infiltration with FDP.

Results:
Transient expression studies show that alpha-farnesene is produced when the alpha-farnesene synthase gene is present but not produced in the control leaves. E,E alpha-farnesene was produced without the addition of the precursor (suggesting that some endogenous precursor is available in the *N. benthamiana* leaves) however, more E,E alpha-farnesene was produced when the precursor was also infiltrated into the leaves. The results are shown in FIG. 15.

Over-expression of apple alpha-farnesene synthase in Arabidopsis: *A. tumefaciens*, strain GV3101, was inoculated into 10 mL of LB media containing rifampicin (10 mg mL$^{-1}$); gentamycin (25 mg mL$^{-1}$); and spectinomycin (100 mg mL$^{-1}$) and grown for 24 hours at 28° C., with shaking at 200 rpm. This starter culture was then used to inoculate a further 100-200 mL of LB media containing antibiotics as above. This was again grown for 24 hours at 28° C., with shaking. The cells were collected by centrifugation (3,500× g, 10 min, 4° C.) and resuspended in 5% sucrose solution, to a final $OD_{600}$ of 0.8. Silwet L-77 was added to a concentration of 0.05%. 45 mL aliquots of these competent *Agro-* bacterium cells were thawed gently on ice. 50-200 ng of plasmid DNA (pHEX2 vector harbouring EST57400) was added to each aliquot and gently mixed, then 40 mL of the cell/plasmid mixture was pipetted into a pre-chilled electroporation cuvette (0.2 cm gap, Bio-Rad). The cells were electroporated using a BioRad GenePulser, on the following settings:
Voltage: 2.5 kV
Capacitance: 25 mFd
Resistance: 400 Ohms The time constant for the pulse was typically 7-9 ms.

The cells were immediately recovered by addition of 1 mL LB media, then decanted into sterile 15 mL centrifuge tubes and incubated at room temperature, with shaking (60 rpm). After 2 hours, 10 mL and 100 mL of the transformed bacteria was spread onto separate LB plates containing rifampicin (10 mg mL$^{-1}$); gentamycin (25 mg mL$^{-1}$); and spectinomycin (100 mg mL$^{-1}$); then grown for 48 hours at 28-30° C.

*A. tumefaciens*, containing the plasmid, was grown in 5 mL cultures of LB media containing rifampicin (10 mg mL$^{-1}$); gentamycin (25 mg mL$^{-1}$); and spectinomycin (100 mg mL$^{-1}$) for 24 hours at 28° C. The cells were collected by centrifugation and resuspended in 5% sucrose solution, to a final OD$_{600}$ of 0.8. Silwet L-77 was added to a concentration of 0.05%.

Healthy five week old *Arabidopsis thaliana* cv Columbia plants, showing a number of immature flower clusters, were transformed with the EST57400 containing or empty vector-containing *Agrobacterium*. The whole of the aboveground portion of the plant was dipped into the *Agrobacterium* suspension, and gently agitated for 3-5 seconds. The dipped plants were then placed in humidity chambers in reduced light for 2-3 days, before being allowed to flower and set seed under normal glasshouse conditions. The seed (T0) was harvested upon complete drying of the plants (5-6 weeks after dipping). T2 seed was generated by selfing plants and growing individuals on kanamycin selection plates over two generations.

DNA extraction: For southern analysis, DNA was extracted from *Arabidopsis thaliana* leaves by the method of Dellaporta et al. Plant Mol. Biol. Reporter 1, 19-21 (1983). Tissue material (1 g) was ground in liquid nitrogen and the powder was added to 15 ml buffer (100 mM Tris-HCl pH 8.0, 50 mM EDTA pH 8.0, 500 mM NaCl) containing 22.5 µl β-mercaptoethanol. After the addition of 1 ml of 20% SDS, the homogenate was touch vortexed and then incubated at 65° C. for 20 minutes. Cold 5 M potassium acetate (5 ml) was added, followed by incubation on ice for 20 minutes and then centrifugation at 6000 rpm for 30 minutes. The supernatant was passed through miracloth, 10 ml cold isopropanol was added and the DNA was left to precipitate overnight at 4° C. The DNA was pelleted by centrifugation at 5000 rpm for 15 minutes, then washed in 1 ml 70% ethanol and resuspended in 0.5 ml water. The resuspended DNA was extracted with an equal volume of 1:1 phenol:chloroform, then extracted with an equal volume of chloroform and reprecipitated with isopropanol. After centrifugation and washing in 70% ethanol the DNA was resuspended in 50 µl water. RNAse (Roche) (1 µl of 10 mg/ml) was added to remove RNA.

For small-scale DNA extractions used in PCR reactions, 150 mg of *Arabidopsis thaliana* leaf tissue was ground in liquid nitrogen. Extraction buffer (480 µl) was added and the tissue was ground further and then left on ice. After adding 37.5 µl of 20% SDS the samples were put at 65° C. for 10 minutes. The samples were mixed by inversion after adding 94 µl of 5 M potassium acetate and then left in ice for 10 minutes before centrifugation at 13,200 rpm for 10 minutes. The supernatant was extracted with 600 µl 25:24:1 phenol:chloroform:isoamyl acetate with gentle mixing and then centrifuged at 10,000 rpm for 5 minutes. 360 µl of isopropanol was added to the supernatant, mixed and then centrifuged for 3 minutes at 13,200 rpm. The pellet was rinsed with 70% ethanol, centrifuged for 1 minute, rinsed with 95% ethanol, air-dried and resuspended in 50 µl TE containing RNAse (Roche).

PCR amplification of DNA PCR amplifications were undertaken using Expand High Fidelity Taq (Roche). Amplification reactions were performed according to the manufacturer's recommendations. The PCR primers (57400_A3 AGAGTTCACTTGCAAGCTGA (SEQ ID NO:3) and 57400_A4 GAAAAGTTCCAGCATTCCTT) (SEQ ID NO:8) were designed to amplify a 513 base pair fragment from the 5' end of the coding region of EST 57400. PCR amplification was performed under the following conditions: denaturation at 96° C. for 5 minutes followed by 30 cycles of denaturation at 96° C. for 30 seconds, annealing at 55° C. for 4 seconds and extension at 72° C. for 60 seconds. The resulting amplification products (5 µl) were analysed by electrophoresis through 1% AppliChem, followed by staining with ethidium bromide and visualisation on an ultraviolet transilluminator (UVP) attached to a camera (UV tec, Total Lab Systems Ltd).

Figure 16:
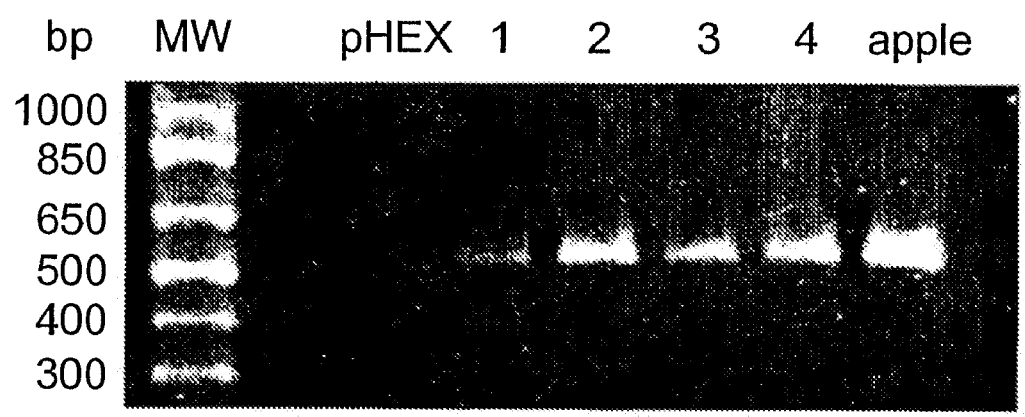
FIG. 16 shows PCR amplification of genomic DNA extracted from transgenic Arabidopsis thaliana plants using primers designed from the 5' end of the alpha-farnesene synthase cDNA sequence. The size of the expected amplification product is 513 bp. The lane labelled MW represents standard molecular weight markers (Invitrogen). Lanes labelled 1, 2, 3 and 4 are independent transgenic Arabidopsis thaliana lines containing the alpha-farnesene synthase cDNA insert. The lane labelled apple shows the amplification product resulting from RT-PCR of total RNA extracted from 'Royal Gala' apple peel.

Results: DNA encoding alpha-farnesene synthase from apple was detected by PCR in each of the four transgenic *Arabidopsis* independent transformants (FIG. 16) and in apple controls. None was detected in the pHEX control.

Southern Analysis

Genomic DNA that had been extracted from *Arabidopsis thaliana* leaf tissue was digested overnight with BamH1 in a total volume of 500 µl. The digested DNA was precipitated with two volumes of ethanol and one-tenth volume of 3M sodium acetate, then centrifuged, washed in 70% ethanol and the pellet resuspended in 30 µl water. The digested DNA was then electrophoresed through 0.7% agarose, visualised with ethidium bromide, hydrolysed in 0.25M HCl and washed in water before transfer to Nytran-Plus (Schleicher & Schuell) membrane in 0.4M NaOH overnight. The membrane was then neutralised in 0.5M Tris and prehybridised in Washing and Pre-Hyb Solution (MRC) for two hours. Hybridisation was performed in 20 ml of High Efficiency Hybridzation System (MRC) using as a probe a $^{32}$P-labelled 810 base pair PCR fragment that was complementary to the 5' end of the coding region of alpha-farnesene synthase. The probe (40 ng) was labelled with $^{32}$P dCTP using the rediprime™II (Amersham Pharmacia) random labelling system, following the manufacturer's directions. The labelled probe was denatured in 0.1 M NaOH for 30 minutes before hybridisation overnight. The membrane was washed in Washing and Pre-Hyb Solution (MRC) according to the manufacturer's recommendations. Hybridisation signals were visualised by scanning on a Storm 840 phosphoimaging system (Molecular Dynamics) and analysed using ImageQuant software.

Figure 17:
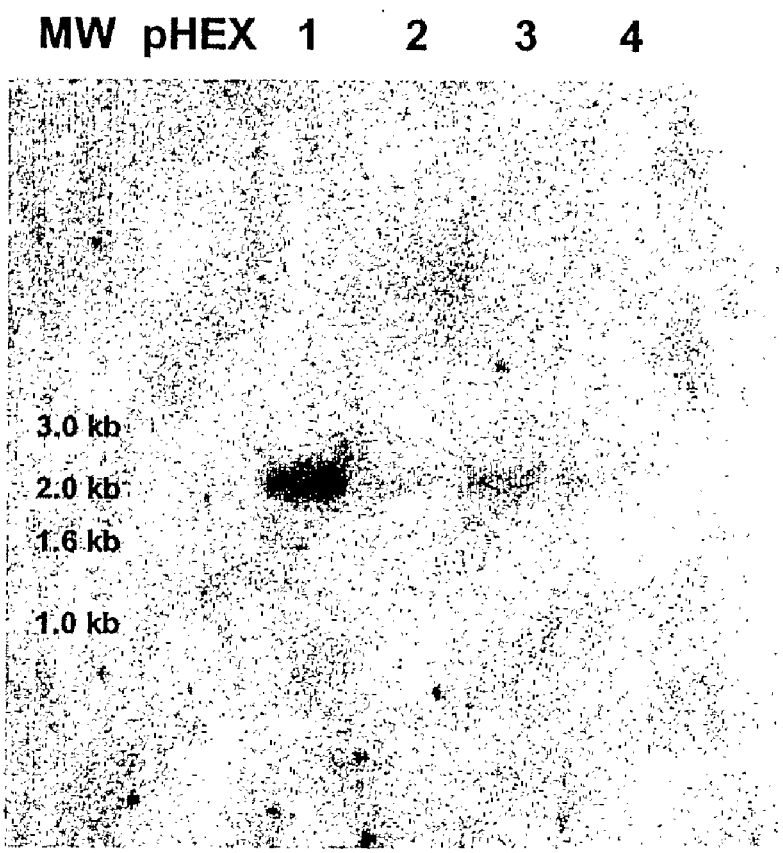
FIG. 17 shows Southern analysis of a BamH1 digest of genomic DNA extracted from transgenic Arabidopsis thaliana plants using as a probe an 810 base pair 32P-labelled PCR fragment that was amplified from EST 57400 with the primers 57400_A3 (5' AGAGTTCACTTG-CAAGCTGA 3' (SEQ ID NO:3)) and 57400NR1 (5' GGAT-GCTTCCCT 3' (SEQ ID NO:4)). The size of the BamH1 restriction fragment containing cDNA for alpha-farnesene synthase is 2050 base pairs. The lane labelled MW is the molecular weight marker (Invitrogen). pHEX is refers to genomic DNA extracted from transgenic Arabidopsis thaliana plants containing the transformation vector only, without the alpha-farnesene synthase cDNA insert. Lanes labelled 1, 2, 3 and 4 are independent transgenic *Arabidopsis thaliana* lines containing the alpha-farnesene synthase cDNA insert. kb=kilobases

Results:

Southern analysis of a BamH1 digest of genomic DNA extracted from transgenic *Arabidopsis thaliana* plants was carried out using as a probe an 810 base pair 32P-labelled PCR fragment that was amplified from EST 57400 with the primers 57400_A3 (5' AGAGTTCACTTGCAAGCTGA 3' SEQ ID NO:3) and 57400NR1 (5' GGATGCTTCCCT 3' (SEQ ID NO:4)). The size of the BamH1 restriction fragment containing cDNA for alpha-farnesene synthase is 2050 base pairs. The results are shown in FIG. 17. The lane labelled MW is the molecular weight marker (Invitrogen). pHEX is refers to genomic DNA extracted from transgenic *Arabidopsis thaliana* plants containing the transformation vector only, without the alpha-farnesene synthase cDNA insert. Lanes labelled 1, 2, 3 and 4 are independent transgenic *Arabidopsis thaliana* lines containing the alpha-farnesene synthase cDNA insert.

Figure 18:
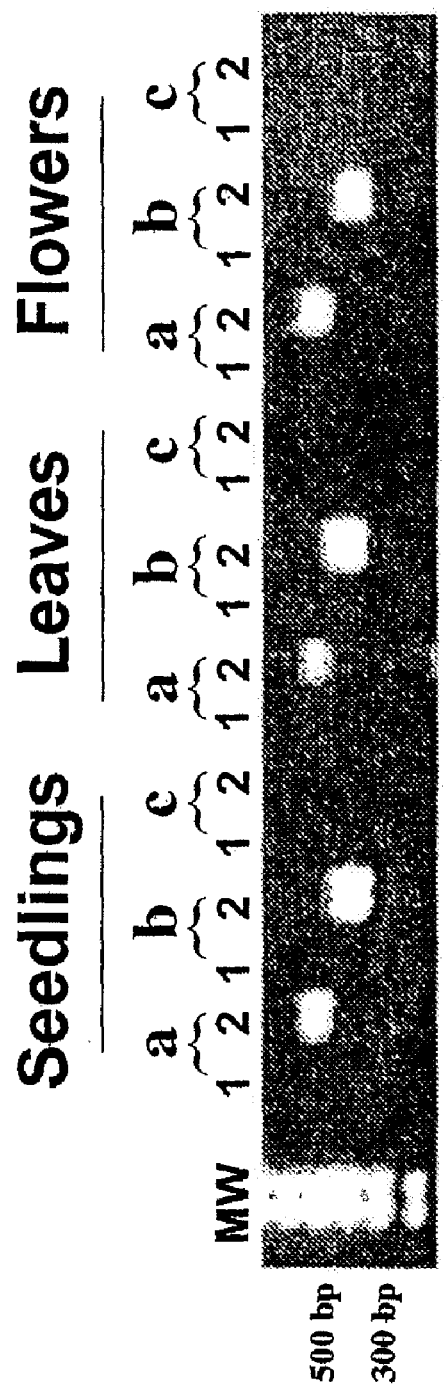
FIG. 18 shows PCR amplification of total RNA extracted from seedlings, leaves and flowers of transgenic *Arabidopsis thaliana* Line 3 plants using primers designed from the 5' end of the alpha-farnesene synthase cDNA sequence (a); from internal sequences (b) and from near the 3' end of the α-farnesene synthase cDNA sequence (c). The size of the amplification product expected for (a) is 513 bp, for (b) is 349 bp and for (c) is 180 bp. The lane labelled MW is the molecular weight marker (Invitrogen). Lanes labelled 1 contain the resulting products from PCR amplification of the total RNA and Lanes labelled 2 contain the resulting products from RT-PCR amplification of the total RNA. bp=base pairs

RT-PCR Amplification:

RT-PCR (Platinum® Quantitative RT-PCR Thermoscript One-Step System, Invitrogen) amplifications were performed according to the manufacturer's recommendations on total RNA extracted from *Arabidopsis thaliana* seedlings, leaves and flowers of Line 3. cDNA synthesis was at 60° C. for 30 minutes, followed by denaturation at 96° C. for 5 minutes, then 40 cycles of amplification involving denaturation at 96° C. for 30 seconds, annealing at 55° C. for 40 seconds and extension at 72° C. for 60 seconds. For the final cycle extension at 72° C. was continued for a further 5 minutes. Prior to RT-PCR the total RNA was treated with DNase I (Life Technologies) for 10 minutes at room temperature. Concurrently with RT-PCR amplification, PCR amplification was also performed on the DNase I-treated total RNA to check for genomic DNA contamination. The PCR primers were as follows: 57400_A3 AGAGTTCACT-TGCAAGCTGA (SEQ ID NO:3) and 57400_A4 GAAAAGTTCCAGCATTCCTT (SEQ ID NO:8), 5' amplification; 57400NF1 GCACATTAGAG AACCACCAT (SEQ ID NO:9) and 57400NR1 GGATGCTTCCCT (SEQ ID NO:4), internal amplification; 57400_A1, CTTCACAA-GAATGAAGATCT (SEQ ID NO:10) and 57400_A5 TTC-CATGCATTGTCTATCAT (SEQ ID NO:11), 3' amplification. The resulting amplification products were analysed as for PCR amplification. The results confirmed the presence of RNA transcripts corresponding to the transgene (see FIG. 18).

*Arabidopsis* Proof of function studies: Approximately 200 T2 generation seeds were measured into a microcentrifuge tube from each of four independent overexpressing lines and one control line. The seed was sterilised in a 1.5% bleach solution containing 0.01% Triton-X, and incubated for 15 min with occasional mixing. The seed was washed several times with distilled water, and resuspended in 0.1% agarose, prior to plating on 0.5X MS media, containing 100 mg/mL kanamycin. The plates were placed into growth rooms with a 12-hour light/12-hour dark cycle. After 2-3 weeks growth 30 plants from each line were transferred to soil in pots and were allowed to continue growing in the glasshouse until mature and producing inflorescences.

Between 30 and 50 inflorescences were harvested before silique appearance and cut ends immediately placed in water. These were then transferred into 55 mL glass tubes with a ground glass joint socket which contained 5 mL distilled water with 25 μM FDP and 7 mM $MgCl_2$. The test-tubes were packed tightly with plant material. The tube was sealed with a ground glass inlet stopper containing a gas line and a volatile sorbent cartridge containing 100 mg Chromosorb 105. The headspace in the flask was purged with dry air at 50 ml $min^{-1}$ while being trapped for 55 hours. The Chromosorb cartridge was dried with a $N_2(g)$ flow at 10 psi, 35 C for 15 min prior to analysis. The volatiles were thermally desorbed and analysed in the same manner as previously described for the apples.

Figure 19:
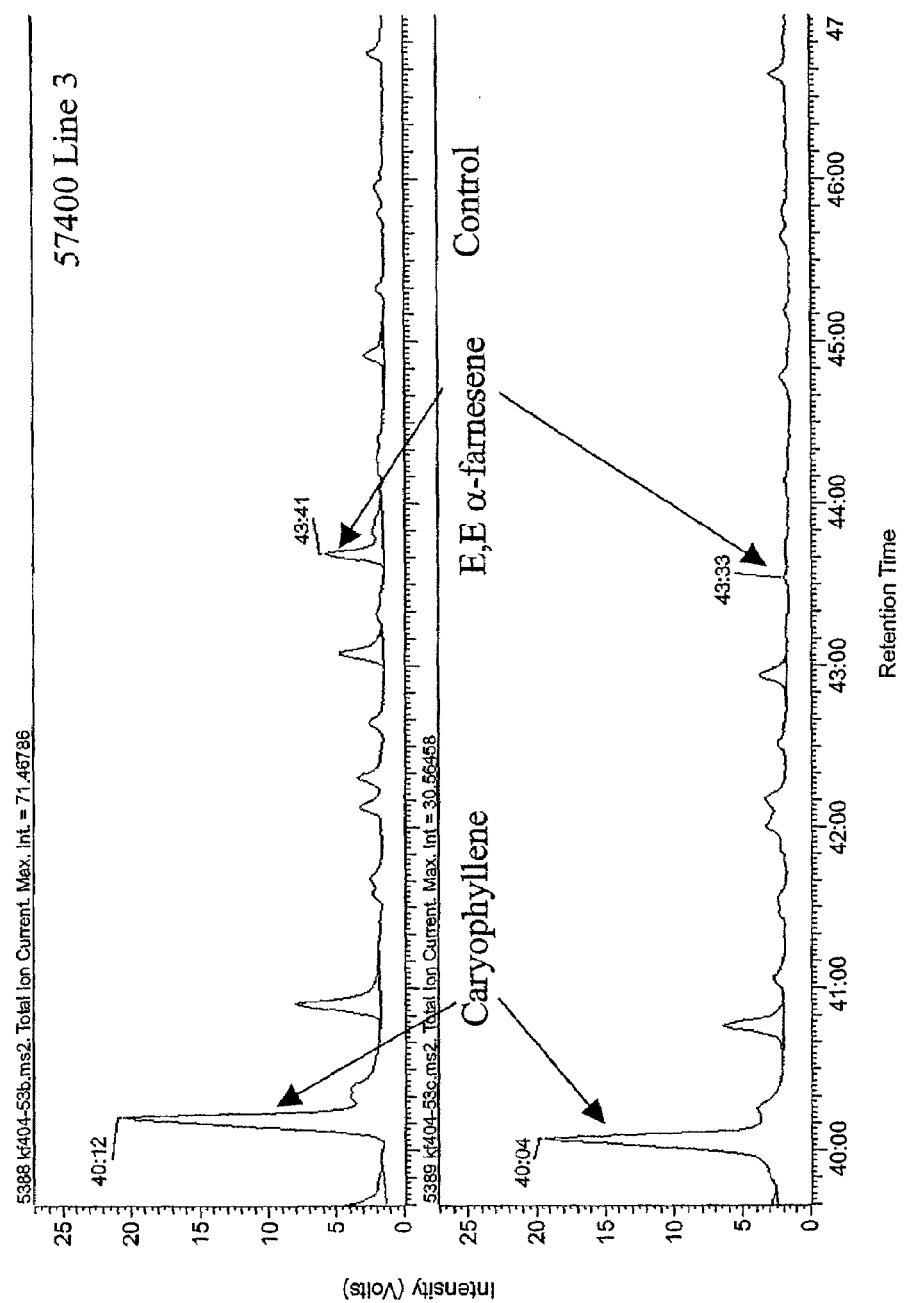
FIG. 19 shows headspace volatiles present in *A. thaliana* inflorescences from Line 3 plants expressing alpha-farnesene synthase gene and from control plants expressing empty vector.

Results: There were a number of sesquiterpene compounds found in the inflorescences of the *Arabidopsis thaliana* plants. The product E, E alpha-farnesene was found in all 4 overexpressing lines of the plants tested and in control pHEX plants. This was confirmed by retention time and comparison of the mass spectra with library spectra. In the 4 lines which had been transformed with EST57400, the ratio of the caryophyllene: alpha-farnesene peak was 3:1, in the pHEX control alpha-farnesene was also present but the ratio of the caryophyllene peak to the alpha-farnesene peak was greater than 10:1. (alpha-farnesene peaks were at 43.33, and 43.41 minutes respectively for pHex, and line 3 see FIG. 19). This suggests that the alpha-farnesene is being produced in small quantities in *A. thaliana* inflorescences along with the other sesquiterpenes but where we have added the gene, alpha-farnesene is being produced in greater proportions than in control plants.

Northern Analysis in Apple ('Royal Gala'):

Methods:

Northern Blot Analysis

Northern analysis was performed as described by Rueger et al. (1996) using antisense RNA probes. Probe templates for alpha-farnesene synthase was prepared by PCR (Genius thermocycler, Techne, Cambridge, UK) plasmid DNA using the following primers:

```
57400NF1
                                         (SEQ ID NO:9)
5-GCACATTAGAGAACCACCAT-3
and 57400NR1
                                        (SEQ ID NO:12)
5-TAATACGACTCACTATAGGGATGCTTCCCTTAAGTTTT-3
```

Final reaction components were as follows: 1×Taq polymerase buffer (Invitrogen), 200 mM dNTPs, 1.5 mM MgCl2, 200 pM of each primer, 50 ng plasmid template or 25 ng genomic DNA, 1 unit Platinum® Taq DNA polymerase in a final volume of 50 mL. PCR conditions included denaturation at 94° C. for 4 min, followed by 25 cycles at 94° C. for 30 seconds, 55° C. for 30 seconds and 72° C. 30 seconds.

Probe transcription reaction for alpha-farnesene synthase was prepared using T7 RNA polymerase (Invitrogen) according to manufacturer's instructions with one modification. The reaction was supplemented with 70 mM DIG-11-UTP (Roche), with UTP reduced to 130 mM. Transcription reactions were incubated at 37° C. for 1 h and then treated with 1 unit of RQ1 RNase free DNase (Promega) in 50 μL total volume for a further 15 min at 37° C. The quantity of RNA probe was calculated by measuring absorbance at 260 nm of a 5 mL aliquot diluted 1:80 in water. The concentration was halved owing to the effect of DIG, and used at the rate of 100 ng probe per mL of hybridisation buffer. Equality of RNA loading was visualised through staining of RNA gels with ethidium bromide, and after probing the blot with an 18S ribosomal RNA PCR product:

```
18S-RFT: CTGGCACCTTATGAGAAATC (SEQ ID NQ:13)

18S-RTR: CCACCCATAGAATCAAGAAA (SEQ ID NO:14)
```

RT-PCR, 55° C. annealing giving a 343 bp product with 40% GC content for 42° C. EasyHyb hybridization.

The level of alpha-farnesene synthase mRNA was adjusted for loading differences calculated from hybridisation of the 18S ribosomal RNA. The resulting signals were analysed using ImageQuant software and a histogram of alpha-farnesene synthase mRNA levels was plotted.

Virtual Northern

ESTs in the HortResearch EST database that were related to alpha-farnesene synthase were identified by using the gene sequence in a BLAST NRDB90 search (Altschul et al., 1997). A 'virtual northern' of the tissues that the EST sequences were found in was produced from an analysis of the cDNA libraries present in the database.

Results:

In a virtual northern, 1 EST was identified among 1000 ESTs in floral buds, 2 from 8050 ESTS in ripe (150 DAFB) apple skin, and 1 with a longer 3' UTR from apple cortex 126 DAFB (days after full bloom) from among 4,500 ESTs. Hence the gene is expressed at relatively low levels during fruit development.

ESTs were identified in mature leaves from three different cultivars, Aotea, Pinkie and senescing Royal Gala leaf. Sequence at the DNA level for all except the ESTs from Aotea and Pinkie were identical to the alpha-farnesene synthase cDNA sequence. No other homologous sequences were detected.

Figure 20:
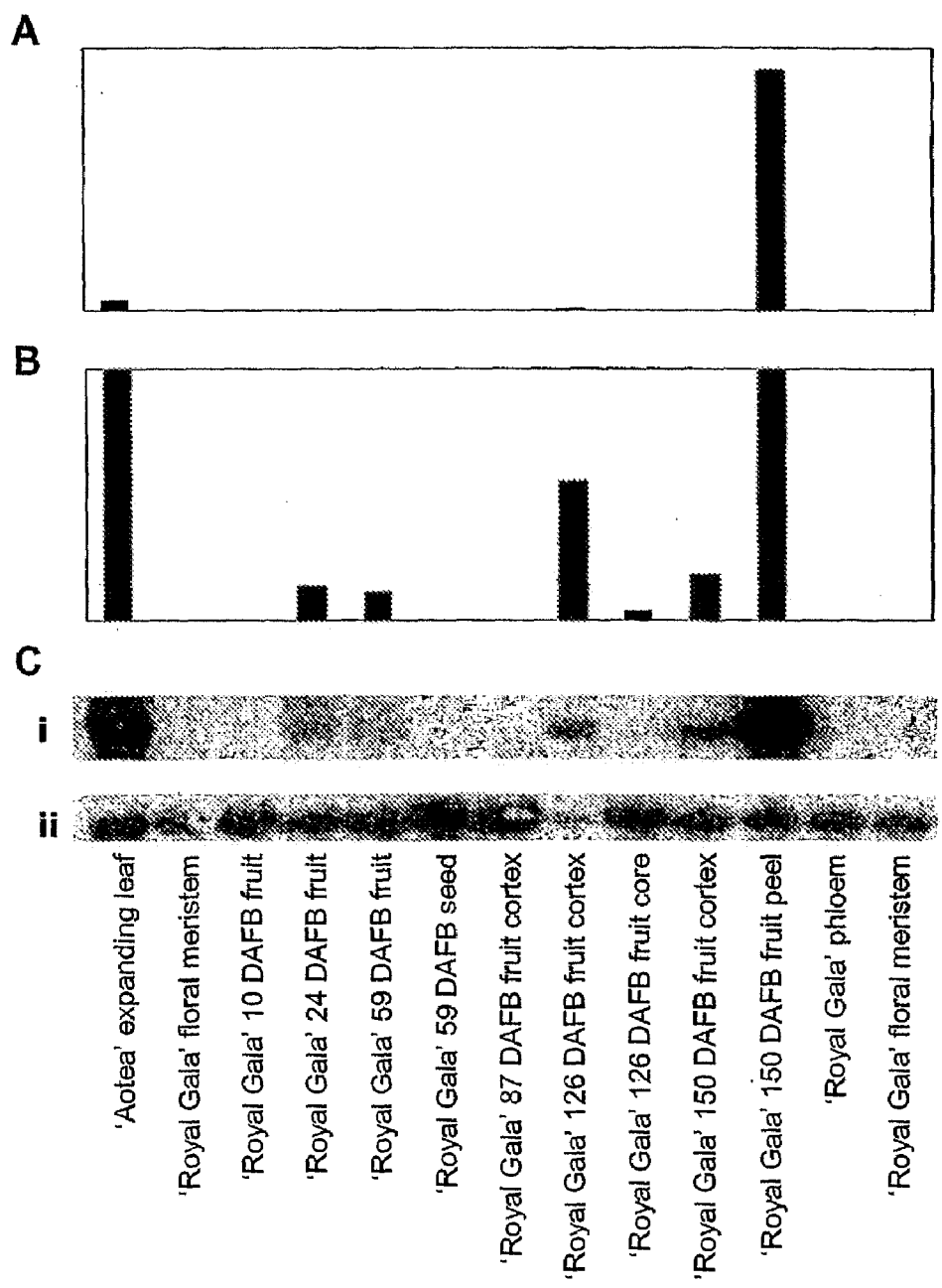
FIG. 20 shows Northern analysis of total RNA extracted from various tissues of *Malus domestica* using as a probe a 350 base pair DIG-labelled PCR fragment that was amplified from EST 57400 with the primers 57400NF1 (5' GCA-CATTAGAGAACCACCAT 3' (SEQ ID NO:5)) and 57400NR1 (5' GGATGCTTCCCT 3' (SEQ ID NO:4)). DAFB=days after full bloom.
A. A histogram of alpha-farnesene synthase mRNA levels that were present in the total RNA extracted from each tissue.
B. A histogram of alpha-farnesene synthase mRNA levels that were present in the total RNA extracted from tissues that are expressing alpha-farnesene synthase at lower levels than in 'Royal Gala' 150 DAFB fruit peel or 'Aotea' expanding leaf
C. i Northern analysis of alpha-farnesene synthase mRNA.
  ii Hybridisation of the 18S ribosomal RNA.

In a standard northern analysis, expression of alpha-farnesene synthase was greatest in skin of ripe fruit (150DAFB) followed by expanding leaf (Aotea) (FIG. 20). The gene was expressed throughout fruit growth, although at lower levels than in ripe fruit skin. mRNA encoding alpha-farnesene synthase was either too low to be detected or not present in floral meristems, phloem and very young fruitlets.

Phylogenetic Analysis:

Computational analysis was performed using the European Molecular Biology Open Software Suite (EMBOSS) (Rice et al., 2000). Sequence identity and similarity was calculated using the pair wise alignment program Needle, which uses the algorithm of Needleman and Wunsch (J. Mol. Biol. 48; 443-453 (1970). The default parameters were used (Gap extension penalty: 0.5 for any sequence; Gap opening penalty: 10 for any sequence). Sequence relatedness was analysed using CLUSTAL X and trimmed and shaded using the program GeneDoc Nicholas and Nicholas, 1997). Phylogenetic trees were used generated in CLUSTAL X using the neighbour-joining method, and the uprooted trees visualised using Treedraw.

Figure 21A:
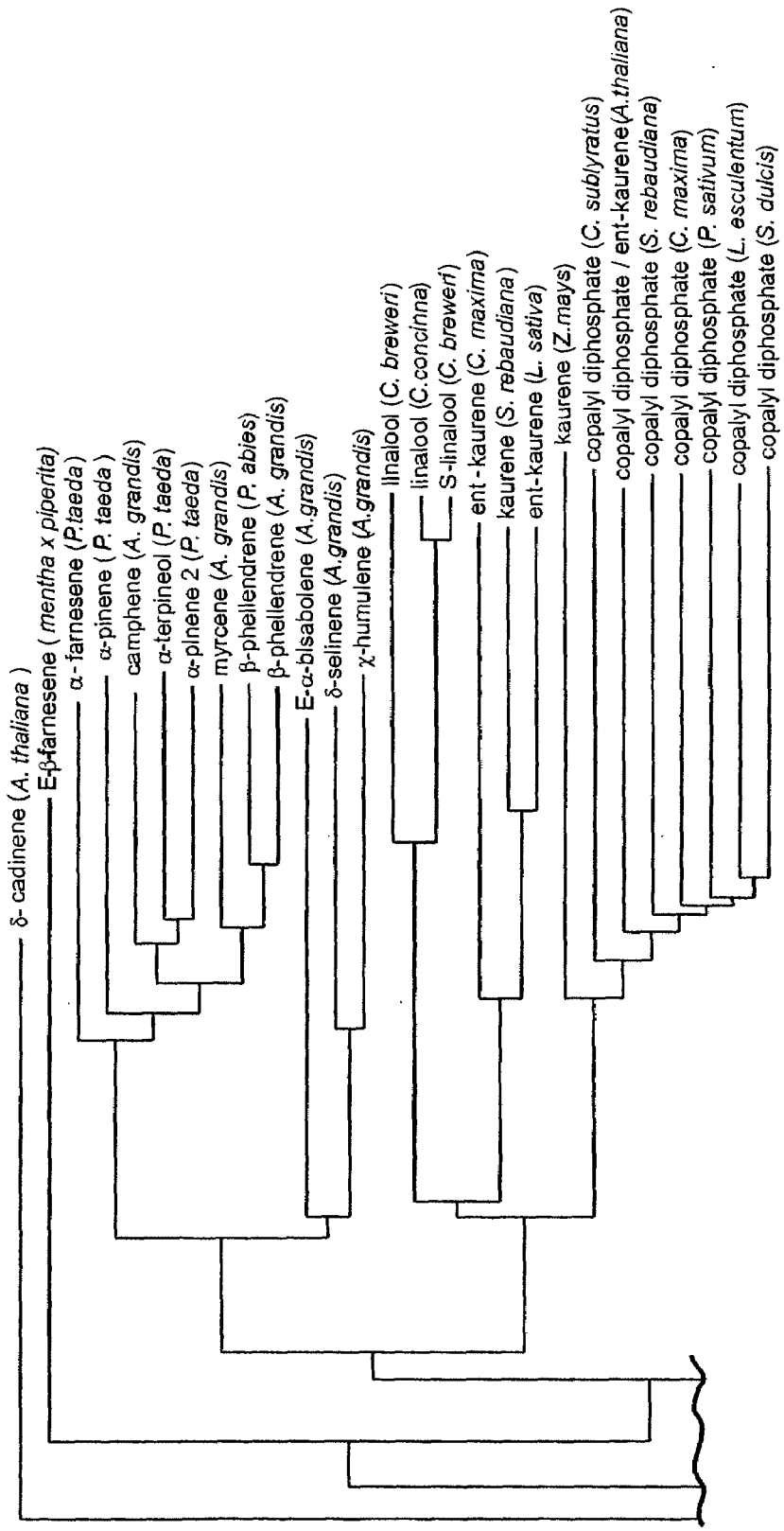
FIGS. 21*a* and 21*b* show a phylogenetic analysis of terpene synthases of known function and shows that alpha-farnesene synthase forms a unique lade.
Figure 21B:
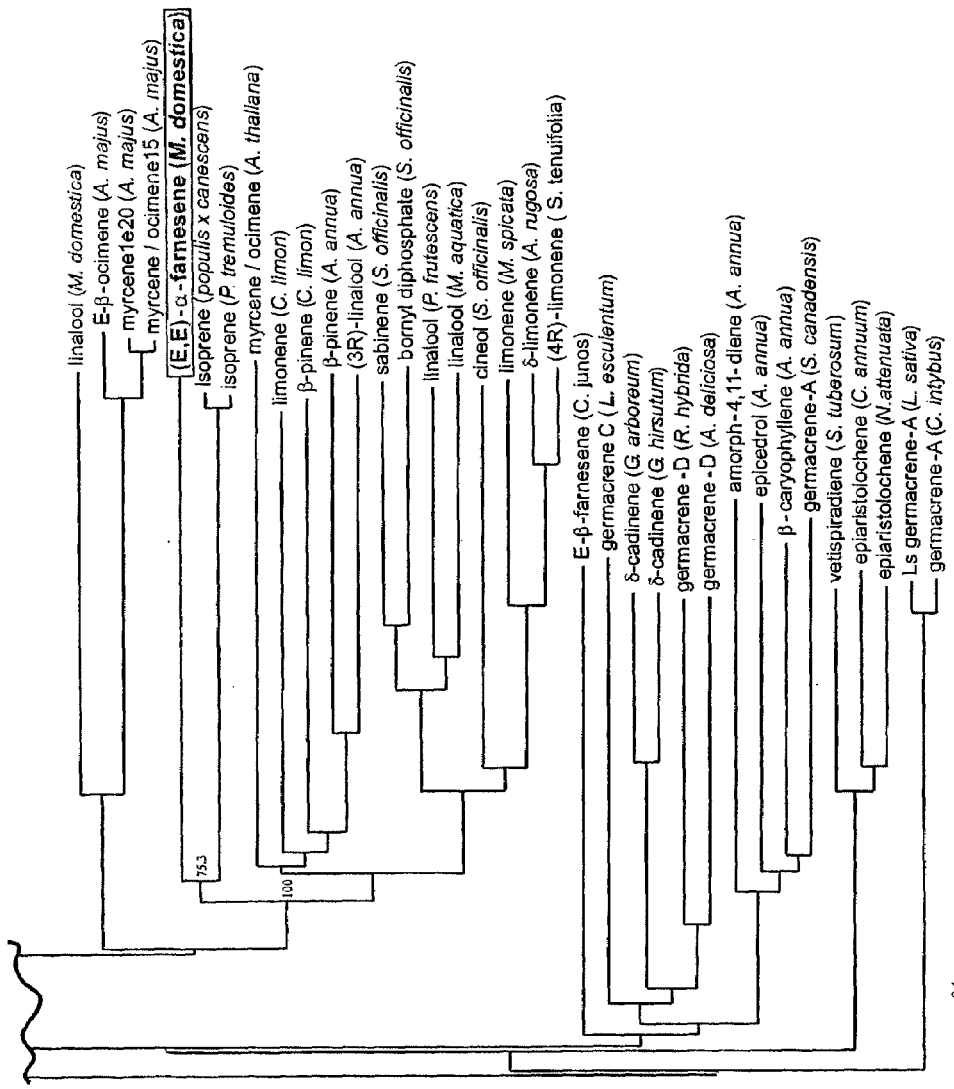

The full length alpha-farnesene synthase was compared to all other terpene synthase sequences of known function (FIGS. 21a and 21b). It formed a clade with a single member, well separated from the nearest homologues, two isoprene synthases from poplar. The separation into its own group reinforces the dissimilarity of the protein sequence to both other sesquiterpene synthases and to monoterpene synthases. A similar result was obtained when only the active site metal binding region around the DDxxD motif was compared across the same set of sequences. In short, this gene would not have been predicted to be a sesquiterpene synthase.

The above Examples illustrate of practice of the invention. It will be appreciated by those skilled in the art that the invention can be carried out with numerous modifications and variations. For example, variations to the nucleotide sequences may be used and the sequences may be expressed in different organisms.

The invention claimed is:

1. An isolated polynucleotide having at least 90% sequence identity to the sequence of SEQ ID NO:1 wherein said polynucleotide encodes a polypeptide with alpha-farnesene synthase activity.

2. The isolated polynucleotide as claimed in claim 1 wherein the sequence has at least 95% identity to the nucleotide sequence of SEQ ID NO:1.

3. The isolated polynucleotide as claimed in claim 1 wherein the nucleotide sequence is that of SEQ ID NO:1.

4. An isolated polynucleotide encoding a polypeptide having at least 90% sequence identity to SEQ ID NO:2, wherein said polypeptide has alpha-farnesene synthase activity.

5. The isolated polynucleotide as claimed in claim 4 wherein the polypeptide has at least 95% identity with the amino acid sequence of SEQ ID NO:2.

6. The isolated polynucleotide as claimed in claim 4 wherein the polypeptide has the sequence of SEQ ID NO:2.

7. A genetic construct comprising the polynucleotide of claim 1.

8. A genetic construct comprising in the 5'-3' direction an open reading frame polynucleotide encoding the polypeptide of claim 1.

9. The genetic construct as claimed in claim 8 further comprising a promoter sequence.

10. The genetic construct as claimed in claim 9 which further comprises a termination sequence.

11. The genetic construct as claimed in claim 10 wherein the sequence of the encoded polypeptide has the amino acid sequence of SEQ ID NO:2 or a fragment thereof with alpha-farnesene activity.

12. A vector comprising the genetic construct of claim 7.

13. A host cell comprising the genetic construct of claim 7.

14. A transgenic plant cell which includes the genetic construct of claim 7.

15. A transgenic plant comprising the plant cell as claimed in claim 14.

* * * * *

SEQUENCE LISTING

<160> NUMBER OF SEQ ID NOS: 14

<210> SEQ ID NO 1
<211> LENGTH: 1952
<212> TYPE: DNA
<213> ORGANISM: Malus domestica

<400> SEQUENCE: 1

```
ctatagcttc ttgtatccca aacatctcga gcttcttgta caccaaatta ggtattcact      60
atggaattca gagttcactt gcaagctgat aatgagcaga aaattttca aaaccagatg      120 aaacccgaac ctgaagcctc ttacttgatt aatcaaagac ggtctgcaaa ttacaagcca      180
aatatttgga agaacgattt cctagatcaa tctcttatca gcaaatacga tggagatgag      240
tatcggaagc tgtctgagaa gttaatagaa gaagttaaga tttatatatc tgctgaaaca      300
atggatttag tagctaagtt ggagctcatt gacagcgtcc gaaaactagg cctcgcgaac      360
ctcttcgaaa aggaaatcaa ggaagcccta gacagcattg cagctatcga aagcgacaat      420
ctcggcacaa gagacgatct ctatggtact gcattacact tcaagatcct caggcagcat      480
ggctataaag tttcacaaga tatatttggt agattcatgg atgaaaaggg cacattagag      540
aaccaccatt tcgcgcattt aaaaggaatg ctggaactt tcgaggcctc aaacctgggt      600
ttcgaaggtg aagatatttt agatgaggcg aaagcttcct tgacgctagc tctcagagat      660
agtggtcata tttgttatcc agacagtaac ctttccaggg acgtagttca ttccctggag      720
cttccatcac accgcagagt gcagtggttt gatgtcaaat ggcaaatcaa cgcctatgaa      780
aaagacattt gtcgcgtcaa cgccacgtta ctcgaattag caaagcttaa tttcaacgta      840
```

-continued

```
gttcaggccc aactccaaaa aaacttaagg gaagcatcca ggtggtgggc aaatctgggc      900
ttcgcagaca acttgaaatt tgcaagagat agactggttg aatgtttctc atgtgctgtg      960
ggagtagcat tcgagcctga gcactcatct tttagaatat gtcttaccaa agtcatcaac     1020
ttagtactga tcatagacga cgtctatgat atttatggct cagaggaaga gctaaagcac     1080
ttcaccaatg ctgttgatag gtgggattct agggaaactg agcagcttcc agagtgtatg     1140
aagatgtgtt ccaagtact ctacaacact acttgtgaaa ttgctcgtga aattgaggag      1200
gagaatggtt ggaaccaagt attacctcaa ttgaccaaag tgtgggcaga ttttttgtaaa    1260
gcattattgg tggaggcaga gtggtataat aagagccata taccaaccct tgaagagtac     1320
ctaagaaacg gatgcatttc atcatcagtt tcagtgcttt tggttcactc gttttctct     1380
ataactcatg agggaaccaa agagatggct gattttcttc acaagaatga agatcttttg     1440
tataatatct ctctcatcgt tcgcctcaac aatgatttgg gaacttccgc ggctgaacaa     1500
gagagagggg attctccttc atcaatcgta tgttacatga gagaagtgaa tgcctctgaa     1560
gaaacagcta ggaagaacat taagggcatg atagacaatg catggaagaa gtaaatggaa    1620
aaatgcttca caacaaacca gtgccttttt ctgtcatcat tcatgaacaa tgccacaaac     1680
atggcacgtg tggcgcacag cctttacaaa gatggagatg ggtttggtga ccaagagaaa    1740
gggcctcgga cccacatcct gtctttacta ttccaacctc ttgtaaacta gtactcatat     1800
agtttgaaat aaatagcagc aagaagtttg cggttcagtt cgtcatggat aaattaatct     1860
ttacagtttg taacgttgtt gcacaaagat tatgaataaa aagttgtagt ttgtcgttta     1920
tttttaaaa aaaaaaaaaa aaaaaaaaaa aa                                    1952
```

<210> SEQ ID NO 2
<211> LENGTH: 576
<212> TYPE: PRT
<213> ORGANISM: Malus domestica

<400> SEQUENCE: 2

```
Met Glu Phe Arg Val His Leu Gln Ala Asp Asn Glu Gln Lys Ile Phe
1               5                  10                  15

Gln Asn Gln Met Lys Pro Glu Pro Glu Ala Ser Tyr Leu Ile Asn Gln
            20                  25                  30

Arg Arg Ser Ala Asn Tyr Lys Pro Asn Ile Trp Lys Asn Asp Phe Leu
        35                  40                  45

Asp Gln Ser Leu Ile Ser Lys Tyr Asp Gly Asp Glu Tyr Arg Lys Leu
    50                  55                  60

Ser Glu Lys Leu Ile Glu Val Lys Ile Tyr Ile Ser Ala Glu Thr
65                  70                  75                  80

Met Asp Leu Val Ala Lys Leu Glu Leu Ile Asp Ser Val Arg Lys Leu
                85                  90                  95

Gly Leu Ala Asn Leu Phe Glu Lys Glu Ile Lys Glu Ala Leu Asp Ser
            100                 105                 110

Ile Ala Ala Ile Glu Ser Asp Asn Leu Gly Thr Arg Asp Asp Leu Tyr
        115                 120                 125

Gly Thr Ala Leu His Phe Lys Ile Leu Arg Gln His Gly Tyr Lys Val
    130                 135                 140

Ser Gln Asp Ile Phe Gly Arg Phe Met Asp Glu Lys Gly Thr Leu Glu
145                 150                 155                 160

Asn His His Phe Ala His Leu Lys Gly Met Leu Glu Leu Phe Glu Ala
                165                 170                 175
```

```
Ser Asn Leu Gly Phe Glu Gly Glu Asp Ile Leu Asp Glu Ala Lys Ala
            180                 185                 190

Ser Leu Thr Leu Ala Leu Arg Asp Ser Gly His Ile Cys Tyr Pro Asp
            195                 200                 205

Ser Asn Leu Ser Arg Asp Val Val His Ser Leu Glu Leu Pro Ser His
            210                 215                 220

Arg Arg Val Gln Trp Phe Asp Val Lys Trp Gln Ile Asn Ala Tyr Glu
225                 230                 235                 240

Lys Asp Ile Cys Arg Val Asn Ala Thr Leu Leu Glu Leu Ala Lys Leu
                245                 250                 255

Asn Phe Asn Val Val Gln Ala Gln Leu Gln Lys Asn Leu Arg Glu Ala
            260                 265                 270

Ser Arg Trp Trp Ala Asn Leu Gly Phe Ala Asp Asn Leu Lys Phe Ala
            275                 280                 285

Arg Asp Arg Leu Val Glu Cys Phe Ser Cys Ala Val Gly Val Ala Phe
            290                 295                 300

Glu Pro Glu His Ser Ser Phe Arg Ile Cys Leu Thr Lys Val Ile Asn
305                 310                 315                 320

Leu Val Leu Ile Ile Asp Asp Val Tyr Asp Ile Tyr Gly Ser Glu Glu
                325                 330                 335

Glu Leu Lys His Phe Thr Asn Ala Val Asp Arg Trp Asp Ser Arg Glu
            340                 345                 350

Thr Glu Gln Leu Pro Glu Cys Met Lys Met Cys Phe Gln Val Leu Tyr
            355                 360                 365

Asn Thr Thr Cys Glu Ile Ala Arg Glu Ile Glu Glu Asn Gly Trp
370                 375                 380

Asn Gln Val Leu Pro Gln Leu Thr Lys Val Trp Ala Asp Phe Cys Lys
385                 390                 395                 400

Ala Leu Leu Val Glu Ala Glu Trp Tyr Asn Lys Ser His Ile Pro Thr
                405                 410                 415

Leu Glu Glu Tyr Leu Arg Asn Gly Cys Ile Ser Ser Ser Val Ser Val
            420                 425                 430

Leu Leu Val His Ser Phe Phe Ser Ile Thr His Glu Gly Thr Lys Glu
            435                 440                 445

Met Ala Asp Phe Leu His Lys Asn Glu Asp Leu Leu Tyr Asn Ile Ser
            450                 455                 460

Leu Ile Val Arg Leu Asn Asn Asp Leu Gly Thr Ser Ala Ala Glu Gln
465                 470                 475                 480

Glu Arg Gly Asp Ser Pro Ser Ser Ile Val Cys Tyr Met Arg Glu Val
                485                 490                 495

Asn Ala Ser Glu Glu Thr Ala Arg Lys Asn Ile Lys Gly Met Ile Asp
            500                 505                 510

Asn Ala Trp Lys Lys Val Asn Gly Lys Cys Phe Thr Thr Asn Gln Val
            515                 520                 525

Pro Phe Leu Ser Ser Phe Met Asn Asn Ala Thr Asn Met Ala Arg Val
            530                 535                 540

Ala His Ser Leu Tyr Lys Asp Gly Asp Gly Phe Gly Asp Gln Glu Lys
545                 550                 555                 560

Gly Pro Arg Thr His Ile Leu Ser Leu Leu Phe Gln Pro Leu Val Asn
                565                 570                 575

<210> SEQ ID NO 3
<211> LENGTH: 20
```

```
<212> TYPE: DNA
<213> ORGANISM: Artificial sequence
<220> FEATURE:
<223> OTHER INFORMATION: Synthetic nucleotide

<400> SEQUENCE: 3
agagttcact tgcaagctga                                                     20

<210> SEQ ID NO 4
<211> LENGTH: 12
<212> TYPE: DNA
<213> ORGANISM: Artificial sequence
<220> FEATURE:
<223> OTHER INFORMATION: Synthetic nucleotide

<400> SEQUENCE: 4
ggatgcttcc ct                                                             12

<210> SEQ ID NO 5
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 5
gcacattaga gaaccaccat                                                     20

<210> SEQ ID NO 6
<211> LENGTH: 676
<212> TYPE: DNA
<213> ORGANISM: Malus domestica

<400> SEQUENCE: 6
ctaagttgga gctcattgac agcgtccgaa aactaggcct cgcgaacctc ttcgaaaagg         60
aaatcaagga agccctagac agcgttgcag ctatcgaaag cgacaatctc ggcacaagag        120
acgatctcta tgctactgca ttacacttca agatcctcag gcagcatggc tataaagttt        180
cacaagatat atttggtaga ttcatggatg aaaagggcac attagagaac caccatttcg        240
cgcatttaaa aggaatgctg aacttttcg aggcctcaaa cctgggtttc gaaggtgaag         300
atattttaga tgaggcgaaa gcttccttga cgctagctct cagagatagt ggtcatattt        360
gttatccaga cagtaacctt tccagggacg tagttcattc cctggagctt ccatcacacc        420
gcagagtgca gtggtttgat gtcaaatggc aaatcgacgc ctatgaaaaa gacatttgtc        480
gcgtcaacgc cacgttactc gaattagcaa agcttaattt caacgtagtt caggcccaac        540
tccaaaaaaa cttaagggaa gcatccaggt ggtgggcaaa cctgggcatc gcagacaact        600
tgaaatttgc aagagataga ctggttgaat gtttcgcatg tgctgtggga gtagcattcg        660
agccagagca ctcatc                                                        676

<210> SEQ ID NO 7
<211> LENGTH: 224
<212> TYPE: PRT
<213> ORGANISM: Malus domestica

<400> SEQUENCE: 7

Lys Leu Glu Leu Ile Asp Ser Val Arg Lys Leu Gly Leu Ala Asn Leu
1               5                   10                  15

Phe Glu Lys Glu Ile Lys Glu Ala Leu Asp Ser Val Ala Ala Ile Glu
            20                  25                  30
```

-continued

```
Ser Asp Asn Leu Gly Thr Arg Asp Asp Leu Tyr Ala Thr Ala Leu His
         35                  40                  45

Phe Lys Ile Leu Arg Gln His Gly Tyr Lys Val Ser Gln Asp Ile Phe
 50                  55                  60

Gly Arg Phe Met Asp Glu Lys Gly Thr Leu Glu Asn His His Phe Ala
 65                  70                  75                  80

His Leu Lys Gly Met Leu Glu Leu Phe Glu Ala Ser Asn Leu Gly Phe
                 85                  90                  95

Glu Gly Glu Asp Ile Leu Asp Glu Ala Lys Ala Ser Leu Thr Leu Ala
                100                 105                 110

Leu Arg Asp Ser Gly His Ile Cys Tyr Pro Asp Ser Asn Leu Ser Arg
            115                 120                 125

Asp Val Val His Ser Leu Glu Leu Pro Ser His Arg Arg Val Gln Trp
130                 135                 140

Phe Asp Val Lys Trp Gln Ile Asp Ala Tyr Glu Lys Asp Ile Cys Arg
145                 150                 155                 160

Val Asn Ala Thr Leu Leu Glu Leu Ala Lys Leu Asn Phe Asn Val Val
                165                 170                 175

Gln Ala Gln Leu Gln Lys Asn Leu Arg Glu Ala Ser Arg Trp Trp Ala
            180                 185                 190

Asn Leu Gly Ile Ala Asp Asn Leu Lys Phe Ala Arg Asp Arg Leu Val
        195                 200                 205

Glu Cys Phe Ala Cys Ala Val Gly Val Ala Phe Glu Pro Glu His Ser
    210                 215                 220
```

<210> SEQ ID NO 8
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 8
gaaaagttcc agcattcctt                    20

<210> SEQ ID NO 9
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 9
gcacattaga gaaccaccat                    20

<210> SEQ ID NO 10
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 10
cttcacaaga atgaagatct                    20

<210> SEQ ID NO 11
<211> LENGTH: 20
<212> TYPE: DNA
<213> ORGANISM: Artificial sequence
<220> FEATURE:
<223> OTHER INFORMATION: Synthetic nucleotide

```
<400> SEQUENCE: 11
ttccatgcat tgtctatcat                                                    20

<210> SEQ ID NO 12
<211> LENGTH: 38
<212> TYPE: DNA
<213> ORGANISM: Artificial sequence
<220> FEATURE:
<223> OTHER INFORMATION: Synthetic nucleotide

<400> SEQUENCE: 12
taatacgact cactataggg atgcttccct taagtttt                                38

<210> SEQ ID NO 13
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 13 ctggcaccttt atgagaaatc                                                   20

<210> SEQ ID NO 14
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 14
ccacccatag aatcaagaaa                                                    20
```